United States Patent [19]
Weinrich et al.

[11] Patent Number: 5,968,506
[45] Date of Patent: Oct. 19, 1999

[54] PURIFIED TELOMERASE

[75] Inventors: Scott L. Weinrich, Redwood City, Calif.; Edward M. Atkinson, III, Seattle, Wash.; Serge P. Lichtsteiner, Cupertino, Calif.; Alain P. Vasserot, Saratoga, Calif.; Ronald A. Pruzan, Palo Alto, Calif.; James T. Kealey, San Anselmo, Calif.

[73] Assignee: Geron Corporation, Menlo Park, Calif.

[21] Appl. No.: 08/833,377

[22] Filed: Apr. 4, 1997

Related U.S. Application Data

[63] Continuation-in-part of application No. 08/510,736, Aug. 4, 1995, abandoned.

[51] Int. Cl.$^6$ .............. A61K 38/51; C12N 9/12; C07H 21/04; A23J 1/00
[52] U.S. Cl. ............ 424/94.5; 435/194; 435/252.3; 435/320.1; 435/91.3; 536/23.2; 935/8; 935/9; 935/14; 530/412; 530/413
[58] Field of Search ............... 424/94.5; 435/194, 435/91.3, 240.1, 254.11, 252.3, 320.1; 536/23.1, 23.2; 935/8, 9, 14; 530/412, 413

[56] References Cited

U.S. PATENT DOCUMENTS 5,583,016  12/1996  Villeponteau ............... 435/91.3

FOREIGN PATENT DOCUMENTS

| WO 95/13382 | 5/1995 | WIPO . | |
| 96/01614 | 1/1996 | WIPO . | |
| 96/01835 | 1/1996 | WIPO | C07H 21/00 |
| WO 96/01835 | 1/1996 | WIPO . | |
| 96/12811 | 5/1996 | WIPO | C12N 15/54 |
| 96/19580 | 6/1996 | WIPO | C12N 15/54 |
| 96/40868 | 12/1996 | WIPO | C12N 5/00 |

OTHER PUBLICATIONS

Counter et al. PNAS, USA. 91: 2900–2904, Apr. 1994.
Feng, Junli et al., "The RNA Component of Human Telomerase," *Science*, vol. 269, No. 5228, Sep. 1, 1995, pp. 1236–1241.
Nomura, Nobou, et al., "Prediction of the Coding Sequences of Unidentified Human Genes," *DNA Research*, vol. 1, 1994, Japan, pp. 27–35.
Srivastava, Meera et al., "Genomic Organization and Chromosomal Localization of the Human Nucleolin Gene," *Journal of Biological Chemistry*, vol. 265, No. 25, 1990, pp. 14922–14931.
Bochnig, P. et al., "A Monoclonal Antibody Against 2,2, 7–trimethylguanosine that reacts with intact class U, small, nuclear ribonucleoproteins as well as with 7–methyl–guanosine–caped RNAs," *Eur.J.Biochem.* 168, pp. 461–467, 1987.
Database WPI, XP002049270 and JP 09 145 575 A (Sosei KK), Section Ch, Week 9734, Derwent Publications, Ltd., GB; Class B04, AN 97–367058, Jun. 17, 1997.
Database WPI XP002049271 and JP 07 242 566 A (Kirin Brewery KK), Section Ch, Week 9546, Derwent Publications, Ltd., London, GB; Class B04, AN 95–355193, Sep. 19, 1995.
M. Singer and D. Gottschling (1994) *Science* 266:404–409. "TLC1: Templates RNA Component of *Saccharomyces cerevisiae* Telomerase".
G. B. Morin (1989) *Cell* 59:521–529. "The Human Telomere Terminal Transferase is a Ribonucleoprotein That Synthesizes TTAGGG Repeats".
Graham et al. (1977) *J. Gen. Virol.* 36: 59–77. "Characteristics of a Human Cell Line Transformed by DNA from Human Adenovirus Type 5".
Stillman and Guzman (1985) *Mol. and Cell Bio.* 5:2051–2060. "Replication and Supercoiling of Simian Virus 40 DNA in Cell Extracts from Human Cells".
E.H. Blackburn (1991) *TIBS* 16:378–381 "Telemeres".
Miller and Rosman (1992) *Biotechniques* 7:980–990. "Improved Retroviral Vectors for Gene Transfer and Expression".
E.H. Blackburn (1992) *Annu. Rev. Biochem.* 61:113–29 "Telomerases".
C.B. Harley (1991) *Mutation Research* 256:271–282. "Telomere loss: mitotic clock or genetic time bomb?".
Romero and Blackburn (1991) *Cell* 67:343–353. "A Conserved Secondary Structure for Telomerase RNA".
J. Lingner et al. (1994) *Genes and Devel.* 8:1984–1988. "Telomerase RNAs of different ciliates have a common secondary and a permuted template".

Primary Examiner—Robert A. Wax
Assistant Examiner—Tekchand Saidha
Attorney, Agent, or Firm—Townsend and Townsend and Crew

[57] ABSTRACT

This invention provides purified human telomerase and methods of purifying it. The methods involve the use of several sequential steps, including the use of a first matrix that binds molecules bearing negative charges, a matrix that binds molecules bearing positive charges, a second matrix that binds molecules bearing negative charges, an affinity purification step and a matrix that separates molecules according to their size.

7 Claims, 7 Drawing Sheets

PURIFIED TELOMERASE

CROSS-REFERENCE TO RELATED APPLICATION

This application is a continuation-in-part of application Ser. No. 08/510,736, filed Aug. 4, 1995.

BACKGROUND OF THE INVENTION

The American population is aging. The fastest growing segment of the population is persons over 85 years of age, who are expected to number over 30 million by the year 2040. This demographic surge is creating significant needs for drugs for the treatment of age-related diseases and has led to increased interest in the aging process and diseases associated with it, including cancer.

Organisms age, in part, because their cells have a finite capacity to continue dividing. As they reach that limit, cells become senescent. Cell senescence has been traced to the ends of a cell's chromosomes, the telomeres. With each cell division, the telomeres lose some DNA and become shorter. At some point this shortening becomes critical. Cells sense this and arrest chromosome replication to avoid further loss. Hence, the cell is no longer able to divide.

Not all cells become senescent. Single-cell organisms and certain mammalian cells have no fixed cell division limit. Investigators have discovered that many of these cells contain a ribonucleoprotein enzyme called telomerase. Telomerase replaces the DNA that is usually lost from the telomeres during cell division. (E. H. Blackburn, (1992) Annu. Rev. Biochem. 61:113–29.) Consequently, the telomeres never shorten past the critical length and the cells never reach senescence.

Particularly interesting, investigators have found that the cells of many human cancers have telomerase. (C. B. Harley, Mutation Research 1991 256:271–282.) This helps explain why cancer cells continue dividing without becoming senescent. It also suggests a potent weapon in the battle against cancer: If telomerase activity in cancer cells can be inhibited, the cancer cells are expected to reach senescence and cease dividing.

Developing methods to regulate telomerase activity requires sources of purified telomerase and, in particular, purified human telomerase. Purified telomerase would be useful in developing and testing assays for measuring telomerase activity, for example, to evaluate the assay and for use as a standard in the assay. Assays for telomerase are useful in characterizing cancer cells or pre-cancer cells, because most cancer cells express telomerase. Purified telomerase would be more useful than crude telomerase preparations to identify and test regulators, inhibitors or activators of telomerase activity in in vitro assays. Moreover, purified telomerase would facilitate a thorough biochemical analysis of the enzyme's mechanism, which may provide insight for development of mechanism-based regulators. Purified telomerase also would be useful in the preparation of antibodies against telomerase. Such antibodies would in turn be especially useful as reagents to purify human telomerase and may be useful in cancer diagnosis or prognosis. Purified telomerase also will help provide amino acid sequence information useful in cloning the various components of the ribonucleoprotein.

While there is a need for purified telomerase, the purification of the human enzyme has posed technical challenges. Telomerase is a rare ribonucleoprotein expressed in human cells only in very low abundance. It has been estimated that human cells known to express the highest levels of telomerase activity may have only about one hundred molecules of the enzyme per cell. The fact that telomerase is a complex, multi-component structure further impedes its purification. Human cells also possess comparatively very high levels of non-telomerase ribonucleoproteins. These other ribonucleoproteins might have chromatographic purification properties similar to the telomerase ribonucleoprotein, which makes purification of telomerase from human cells difficult. Thus, there is a need for purified telomerase and purified human telomerase, in particular.

SUMMARY OF THE INVENTION

Human telomerase has been purified to over 60,000-fold purity over cytoplasmic crude cell preparations. Two polypeptides that co-purify with fractions containing telomerase activity are present in the purified fractions in approximate stoichiometric amounts with the RNA component of human telomerase have been isolated. One polypeptide has amino and sequences consistent with nucleolin. The other polypeptide has amino acid sequences consistent with elongation factor 2 homolog.

In one aspect, this invention provides methods of purifying telomerase. The steps included in the method depend on the level of purification one desires. A method to purify telomerase from an impure composition containing organic biomolecules, for example, a nuclear extract of 293 cells, to at least 60,000-fold compared to crude extract (about 4% relative purity) involves:

(1) contacting the telomerase with a first matrix that binds molecules bearing a negative charge, for example, POROS® 50 HQ, separating telomerase from other organic biomolecules that do not bind to the matrix and collecting the telomerase;

(2) contacting the telomerase with a matrix that binds molecules bearing a positive charge, for example POROS® Heparin 20 HE-1, separating telomerase from other organic biomolecules that do not bind to the matrix and collecting the telomerase;

(3) contacting the telomerase with a second matrix that binds molecules bearing a negative charge, for example, SOURCE 15Q®, separating telomerase from other organic biomolecules that do not bind to the matrix and collecting the telomerase;

(4) contacting the telomerase with an affinity agent having specific affinity for telomerase, for example an oligonucleotide having the sequence 5'-cgttcctctt cctgcggcct-3' (Oligo 14ab) (SEQ ID NO:7), separating telomerase from other organic biomolecules that do not bind to the affinity agent and collecting the telomerase; and (5) separating the telomerase from other organic biomolecules according to molecular size, shape, or buoyant density, for example separating molecules according to size on a TosoHaas TSK-gel*G5000PW$_{XL}$ sizing column and collecting the telomerase.

Telomerase can be isolated to at least 500,000-fold purity by adding a second affinity step using anti-nucleolin antibodies or anti-TMG antibodies. Telomerase can be purified to substantial purity (e.g., at least 1,000,000-fold) by further isolating it by gel electrophoresis.

The purification protocol also can include the step of contacting the telomerase with an intermediate-selectivity matrix, separating telomerase from other organic biomolecules that do not bind to the intermediate-selectivity matrix and collecting the telomerase, preferably before the affinity step.

Telomerase can be isolated to different levels of purity by altering, changing the sequence of, or eliminating any of the steps in the purification protocol. However, any protocol will include contacting the telomerase with an affinity agent. Contacting the telomerase with at least one matrix that binds molecules bearing a negative charge or a positive charge is the next preferred step or steps to include in the protocol.

The invention also provides purified telomerase and, more particularly, telomerase having at least 2000-fold, at least 3000-fold, at least 20,000-fold, at least 60,000-fold, at least 100,000-fold, at least 500,000-fold or at least 1,000,000-fold increased relative purity compared to crude cell extracts of 293 cells. The telomerase can be animal, mammalian and, more particularly, human. The invention also provides telomerase made by the purification steps above, or recombinantly.

In another aspect, this invention provides a recombinant polynucleotide comprising a nucleotide sequence that encodes a polypeptide having at least 5 consecutive amino acids of a protein component of human telomerase. In one embodiment the recombinant polynucleotide further comprises an expression control sequence operatively linked with the nucleotide sequence.

In another aspect, this invention provides a polynucleotide probe or primer that specifically hybridizes with a polynucleotide encoding a protein component of human telomerase.

In another aspect, this invention provides a recombinant cell comprising a recombinant polynucleotide comprising an expression control sequence operatively linked to a nucleotide sequence encoding a protein component of mammalian telomerase, wherein the cell produces the RNA and protein components of telomerase core enzyme. In one embodiment, the recombinant cell further comprises a recombinant polynucleotide that comprises an expression control sequence operably linked to a nucleotide sequence encoding the RNA component of telomerase. This invention provides a method of making recombinant telomerase comprising culturing a recombinant cell of this invention.

In another aspect this invention provides a composition comprising recombinant human telomerase made by the methods of this invention.

In another aspect this invention provides methods of inducing an immune response against telomerase comprising inoculating an animal with purified telomerase or with an immunogenic fragment thereof, such as a protein component. This includes induction of a humoral immune response that leads to the production of antibodies, as well as a cell-mediated immune response.

In another aspect this invention also provides a polypeptide fragment of a protein component of human telomerase which, when presented to an animal as an immunogen, elicits a humoral or cell-mediated immune response.

In another aspect, this invention provides a composition comprising an antibody or antibody fragment that specifically binds to a protein component of human telomerase.

DETAILED DESCRIPTION OF THE INVENTION

I. DEFINITIONS

Figure 1:
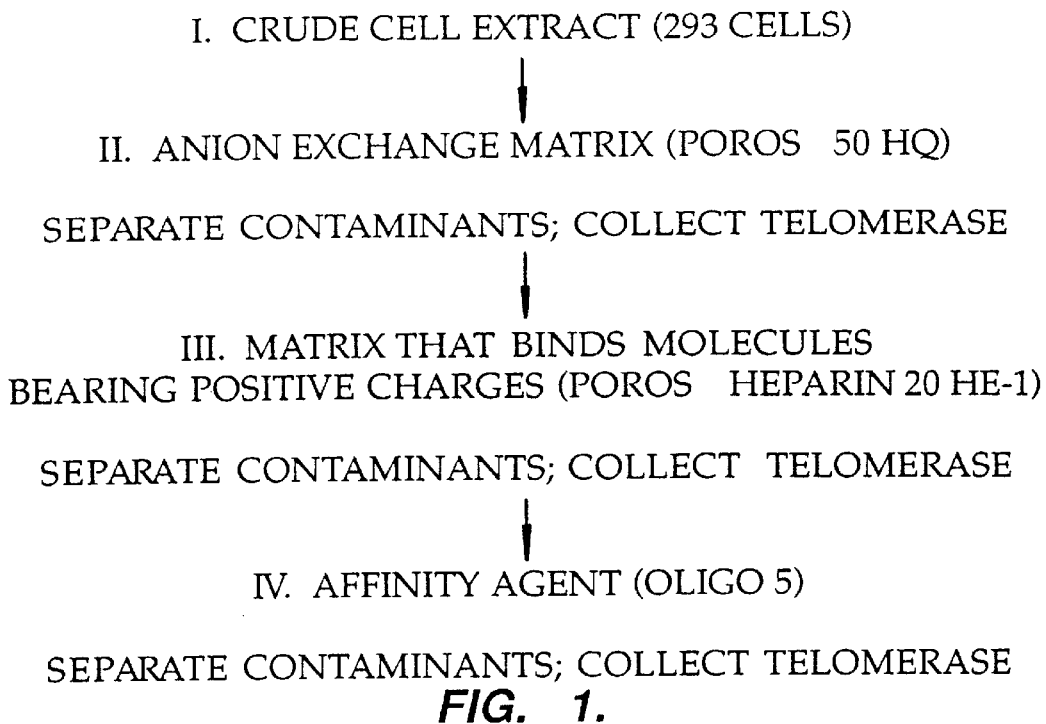
FIG. 1 depicts a four-step protocol for purifying telomerase.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). As used herein, the following terms have the meanings ascribed to them unless specified otherwise.

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide nucleic acids ("PNAs"), and the like. Such polynucleotides can be synthesized, for example, using an automated DNA synthesizer. "Nucleic acid" typically refers to large polynucleotides. "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well. Appropriate unicellular hosts include any of those routinely used in expressing eukaryotic or mammalian nucleic acids, including, for example, prokaryotes, such as E. coli; and eukaryotes, including for example, fungi, such as yeast; and mammalian cells, including insect cells (e.g., Sf9) and animal cells such as CHO, R1.1, B-W, L-M, African Green Monkey Kidney cells (e.g. COS 1, COS 7, BSC 1, BSC 40 and BMT 10) and cultured human cells.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

"Hybridizing specifically to" or "specific hybridization" or "selectively hybridize to," refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2× SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1× SSC at 45° C. for 15 minutes. An example low stringency wash for a duplex of, e.g., more than 100 nucleotides, is 4–6× SSC at 40° C. for 15 minutes. In general, a signal-to-noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies.

An antibody "specifically binds to" or "is specifically immunoreactive with" a protein when the antibody functions in a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual,* Cold Spring Harbor Publications, New York, for a description of immunoassay formats and conditions that can be used to determine specific immunoreactivity.

"Immunoassay" refers to an assay that utilizes an antibody to specifically bind an analyte. The immunoassay is characterized by the use of specific binding properties of a particular antibody to isolate, target, and/or quantify the analyte.

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Substantially pure" means an object species is the predominant species present (i.e., on a molar basis, more abundant than any other individual organic biomolecular species in the composition), and a substantially purified fraction is a composition wherein the object species comprises at least about 50% (on a molar basis) of all organic biomolecular species present. Generally, a substantially pure composition means that about 80% to 90% or more of the organic biomolecular species present in the composition is the purified species of interest. The object species is purified to essential homogeneity (contaminant species cannot be detected in the composition by conventional detection methods) if the composition consists essentially of a single organic biomolecular species. "Organic biomolecule" refers to an organic molecule of biological origin, e.g., proteins, nucleic acids, carbohydrates or lipids. Solvent species, small molecules (<500 Daltons), stabilizers (e.g., BSA), and elemental ion species are not considered organic biomolecular species for purposes of this definition.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Telomerase" or "telomerase ribonucleoprotein complex" refers to a ribonucleoprotein enzyme of eukaryotic origin identifiable by its ability to polymerize a DNA sequence of a eukaryotic telomere. Telomerase is further characterized by an RNA component having sequences complementary to at least part of the telomeric repeat of the source species and by one or more protein components. As used herein, "animal telomerase," "mammalian telomerase" and "human telomerase" refer to telomerases that can be found naturally in various multicellular animal, mammalian or human cells, respectively, or having polypeptide components with the same amino acid sequences, and RNA components with the same nucleotide sequences. Human telomerase contains the RNA component, "hTR." (U.S. Pat. No. 5,583,016, Villeponteau et al.) The term "telomerase" includes all allelic forms of telomerase, including wild-type and mutant forms.

"Telomerase protein component" refers to a protein component of the telomerase core enzyme.

"Telomerase core enzyme" refers to the assembled collection of telomerase components, both the RNA and protein components, sufficient for telomerase activity in vitro.

"Telomerase associated protein" refers to a protein that binds to the telomerase core enzyme but that is not necessary for telomerase activity in vitro.

"Telomerase activity factor" refers to a protein which, when included with telomerase core enzyme, improves telomerase activity in vitro.

"Telomerase related protein" refers, collectively, to telomerase protein components, telomerase associated proteins and telomerase activity factors.

"Telomerase activity" refers to the synthesis of telomeric DNA by telomerase. One assay method for detecting telomerase activity is the TRAP assay. See Harley et al., International Application WO 95/13381. This assay measures the amount of radioactive nucleotides incorporated into elongation products, polynucleotides, formed by nucleotide addition to a telomerase substrate or primer. The radioactivity incorporated can be measured as a function of the intensity of a band on a PhosphorImager™ screen exposed to a gel on which the radioactive products are separated. A test experiment and a control experiment can be compared by visually using the PhosphorImager™ screens. See also the commercially available TRAP-eze™ telomerase assay kit (Oncor); and Morin, *Cell* 59: 521–529 (1989).

The "specific activity" of telomerase is the amount of telomerase activity per amount of protein in a unit volume.

"Purified telomerase" refers to telomerase preparations having at least 2000-fold increased relative purity. As used herein, a telomerase preparation has 2000-fold increased relative purity if the specific activity of telomerase in the preparation is at least 2000 times greater than the specific activity of telomerase of crude cytoplasmic extracts of suspension-capable 293 cells, described herein below, and as measured by the primer elongation assay described herein below in Example I.A. It is estimated that in a telomerase preparation having about 100,000-fold increased relative purity, about 6% of the proteins are telomerase, while in a telomerase preparation having about 1,000,000-fold increased relative purity, about 60% of the protein molecules are telomerase.

II. METHODS OF PURIFYING TELOMERASE

This invention provides purified telomerase and methods of making it. In particular, this invention is directed to purified mammalian or human telomerase and recombinant telomerase. This invention provides purified telomerase isolated from any cells expressing telomerase, for example, crude extracts of normal cells, cancer cells, immortalized cells, human or animal tissues, tumors, or from cells expressing telomerase recombinantly.

A. Assays for Telomerase Activity

In methods of purifying telomerase it is often useful to determine the presence or amount of telomerase or telomerase activity in a preparation. Several assays are available for this. As stated above, for the purpose of determining relative purity, the most preferred method of measuring the specific activity of telomerase is the primer elongation assay. This assay is described in Example I.A, below. Briefly, this assay measures the amount of radioactive nucleotides incorporated into polynucleotides synthesized on a primer sequence. The amount incorporated is measured as a function of the intensity of a band on a phosphoimager screen exposed to a gel on which the radioactive products are separated. A test experiment and a control experiment can be compared by eye on phosphoimager screens. This assay is based on an assay described by G. B. Morin, (1989) *Cell* 59:521–529.

Another assay for telomerase activity is the dot blot assay. The dot blot assay is useful for routine screening because it has high throughput and hundreds of assays can be carried out in a single day with a good portion of the labor performed automatically. Results are available by the afternoon of the second day. The dot blot assay is most effective for comparing activity of samples at roughly the same level of purity and less effective for samples at different stages of purity. Therefore, it is not a preferred assay for determining relative purity. A protocol for the dot blot assay is provided in Example I.B.

Other assays involve detecting the presence of the RNA component of telomerase. The sequence of the RNA component of telomerase for several species is known. A polynucleotide comprising the sequence for the RNA component of human telomerase ("hTR") has been isolated. Human genomic DNA encoding hTR has been cloned, sequenced and placed on deposit. A lambda clone designated "28-1" contains an ~15 kb insert containing human telomerase RNA component gene sequences. Clone 28-1 was deposited with the American Type Culture Collection pursuant to the Budapest Treaty and granted accession number ATCC 75925. Plasmid pGRN33 contains an ~2.5 kb HindIII-SacI insert containing sequences from lambda clone 28-1 that contain the sequence of hTR. Plasmid pGRN33 was deposited with the American Type Culture Collection pursuant to the Budapest Treaty and granted accession number ATCC 75926. A PstI fragment of the ~2.4 kb SauIIIA1-HindIII fragment of clone 28-1 also contains the hTR sequence. The sequence of the PstI fragment is provided in SEQ ID NO: 1, below. The nucleotides of hTR are indicated above the sequence indicated by stars and numbered 1 to 451. The template region is underlined.

```
                         #                                          (SEQ ID NO:1)
    1 CTGCAGAGGATAGAAAAAAG0CCCTCTGATACCTCAAGTTAGTTTCACCTTTAAAGAAGG
      GACGTCTCCTATCTTTTTTC7GGGAGACTATGGAGTTCAATCAAAGTGGAAATTTCTTCC
      -P_ST1-

61 TCGGAAGTAAAGACGCAAAGCCTTTCCCGGACGTGCGGAAGGGCAACGTCCTTCCTCATG
      AGCCTTCATTTCTGCGTTTCGGAAAGGGCCTGCACGCCTTCCCGTTGCAGGAAGGAGTAC

121 GCCGGAAATGGAACTTTAATTTCCCGTTCCCCCCAACCAGCCCGCCCGAGAGAGTGACTC
      CGGCCTTTACCTTGAAATTAAAGGGCAAGGGGGGTTGGTCGGGCGGGCTCTCTCACTGAG

181 TCACGAGAGCCGCGAGAGTCAGCTTGGCCAATCCGTGCGGTCGGCGGCCGCTCCCTTTAT
      AGTGCTCTCGGCGCTCTCAGTCGAACCGGTTAGGCACGCCAGCCGCCGGCGAGGGAAATA 1         10        20        30
                             ********************************
  241 AAGCCGACTCGCCCGGCAGCGCACCGGGTTGCGGAGGGTGGGCCTGGGAGGGTGGTGGC
      TTCGGCTGAGCGGGCCGTCGCGTGGCCCAACGCCTCCCACCCGGACCCTCCCCACCACCG 40        50        60        70        80        90
                            ************************************************
  301 CATTTTTTGTCTAACCCTAACTGAGAAGGGCGTAGGCGCCGTGCTTTTGCTCCCCGCGCG
      GTAAAAAACAGATTGGGATTGACTCTTCCCGCATCCGCGGCACGAAAACGAGGGCGCGC 100       110       120       130       140       150
                           ************************************************
  361 CTGTTTTTCTCGCTGACTTTCAGCGGGCGGAAAAGCCTCGGCCTGCCGCCTTCCACCGTT
      GACAAAAAGAGCGACTGAAAGTCGCCCGCCTTTTCGGAGCCGGACGGCGGAAGGTGGCAA 160       170       180       190       200       210
                           ************************************************
  421 CATTCTAGAGCAAACAAAAAATGTCAGCTGCTGGCCCGTTCGCCCCTCCCGGGGACCTGC
      GTAAGATCTCGTTTGTTTTTTACAGTCGACGACCGGGCAAGCGGGAGGGCCCCTGGACG
```

```
                              hTR
            220       230       240       250       260       270
            ************************************************************
       481  GGCGGGTCGCCTGCCCAGCCCCCGAACCCCGCCTGGAGGCCGCGGTCGGCCCGGGGCTTC
            CCGCCCAGCGGACGGGTCGGGGGCTTGGGGCGGACCTCCGGCGCCAGCCGGGCCCCGAAG 280       290       300       310       320       330
            ************************************************************
       541  TCCGGAGGCACCCACTGCCACCGCGAAGAGTTGGGCTCTGTCAGCCGCGGGTCTCTCGGG
            AGGCCTCCGTGGGTGACGGTGGCGCTTCTCAACCCGAGACAGTCGGCGCCCAGAGAGCCC 340       350       360       370       380       390
            ************************************************************
       601  GGCGAGGGCGAGGTTCAGGCCTTTCAGGCCGCAGGAAGAGGAACGGAGCGAGTCCCCGCG
            CCGCTCCCGCTCCAAGTCCGGAAAGTCCGGCGTCCTTCTCCTTGCCTCGCTCAGGGGCGC 400       410       420       430       440       450
            *********************************************************
       661  CGCGGCGCGATTCCCTGAGCTGTGGGACGTGCACCCAGGACTCGGCTCACACATGCAGTT
            GCGCCGCGCTAAGGGACTCGACACCCTGCACGTGGGTCCTGAGCCGAGTGTGTACGTCAA

721  CGCTTTCCTGTTGGTGGGGGGAACGCCGATCGTGCGCATCCGTCACCCCTCGCCGGCAGT
            GCGAAAGGACAACCACCCCCCTTGCGGCTAGCACGCGTAGGCAGTGGGGAGCGGCCGTCA

781  GGGGGCTTGTGAACCCCCAAACCTGACTGACTGGGCCAGTGTGCTGCAAATTGGCAGGAG
            CCCCCGAACACTTGGGGGTTTGGACTGACTGACCCGGTCACACGACGTTTAACCGTCCTC

841  ACGTGAAGGCACCTCCAAAGTCGGCCAAAATGAATGGGCAGTGAGCCGGGGTTGCCTGGA
            TGCACTTCCGTGGAGGTTTCAGCCGGTTTTACTTACCCGTCACTCGGCCCCAACGGACCT

901  GCCGTTCCTGCGTGGGTTCTCCCGTCTTCCGCTTTTTGTTGCCTTTTATGGTTGTATTAC
            CGGCAAGGACGCACCCAAGAGGGCAGAAGGCGAAAAACAACGGAAAATACCAACATAATG

961  AACTTAGTTCCTGCTCTGCAG
            TTGAATCAAGGACGAGACGTC
                              -P_{St}1-
       (# = "7" IS A OR T)
```

For the sequence of the RNA component of telomerase of humans, mice, yeast and ciliates see Feng et al. (1995) *Science* 269:1236–41; Villeponteau et al., U.S. Pat. No. 5,583,016; WO 96/01835 (Villeponteau et al.), WO 96/01604 (Andrews et al.), Blasco et al. (1995) *Science* 269:1267–1270; Romero and Blackburn (1991) *Cell* 67:343–353; Lingner et al. (1994) *Genes and Devel.* 8:1984–1988; and Singer and Gottschling (1994) *Science* 266:404–409.

Reverse transcription PCR ("RT-PCR") is a useful assay for determining the amount of telomerase RNA because it is very sensitive. A protocol for an RT-PCR assay is provided in Example I.C. See also, U.S. patent application Ser. No. 08/770,565, filed Dec. 20, 1996. Other methods for specific RNA detection can be used, for instance, Northern Analysis. A protocol for a Northern Analysis is provided in Example I.D. The major limitation of using any of the hTR assays to detect telomerase is that the presence of hTR does not mean that active telomerase is present. For example, normal somatic cells and some fractions from partially purified telomerase have significant quantities of hTR but no detectable telomerase activity.

Another very sensitive assay for telomerase activity is the TRAP assay, described in Harley et al., International publication WO 95/13381; Harley et al., International application PCT/US96/09669, filed Jun. 7, 1996 and Kim et al. (1994) *Science* 266:2011–2015.

B. Purification Protocols

1. General Considerations

This invention provides methods of making purified telomerase from an impure composition, i.e., a composition containing telomerase and other contaminating organic biomolecules. Beginning with an impure telomerase composition, a method that yields telomerase that is over 60,000-fold pure involves the following steps:

(1) providing an impure preparation containing telomerase, for example, a nuclear extract;

(2) isolating telomerase from other organic biomolecules with a first matrix that binds molecules bearing a negative charge, for example, POROS® 50 HQ;

(3) further purifying the telomerase with a matrix that binds molecules bearing a positive charge, for example POROS® Heparin 20 HE-1;

(4) further purifying the telomerase with a second matrix that binds molecules bearing a negative charge, for example, SOURCE 15Q®, (5) further purifying the telomerase with an affinity agent having specific affinity for telomerase, for example the oligonucleotide 14ab, which has the sequence 5'-cgttcctctt cctgcggcct-3' (SEQ ID NO:7); and (6) further purifying the telomerase from other organic biomolecules according to molecular size, shape, or buoyant density, for example separating molecules according to size on a TosoHaas TSK-Gel*G5000PW$_{XL}$ sizing column.

Figure 2:
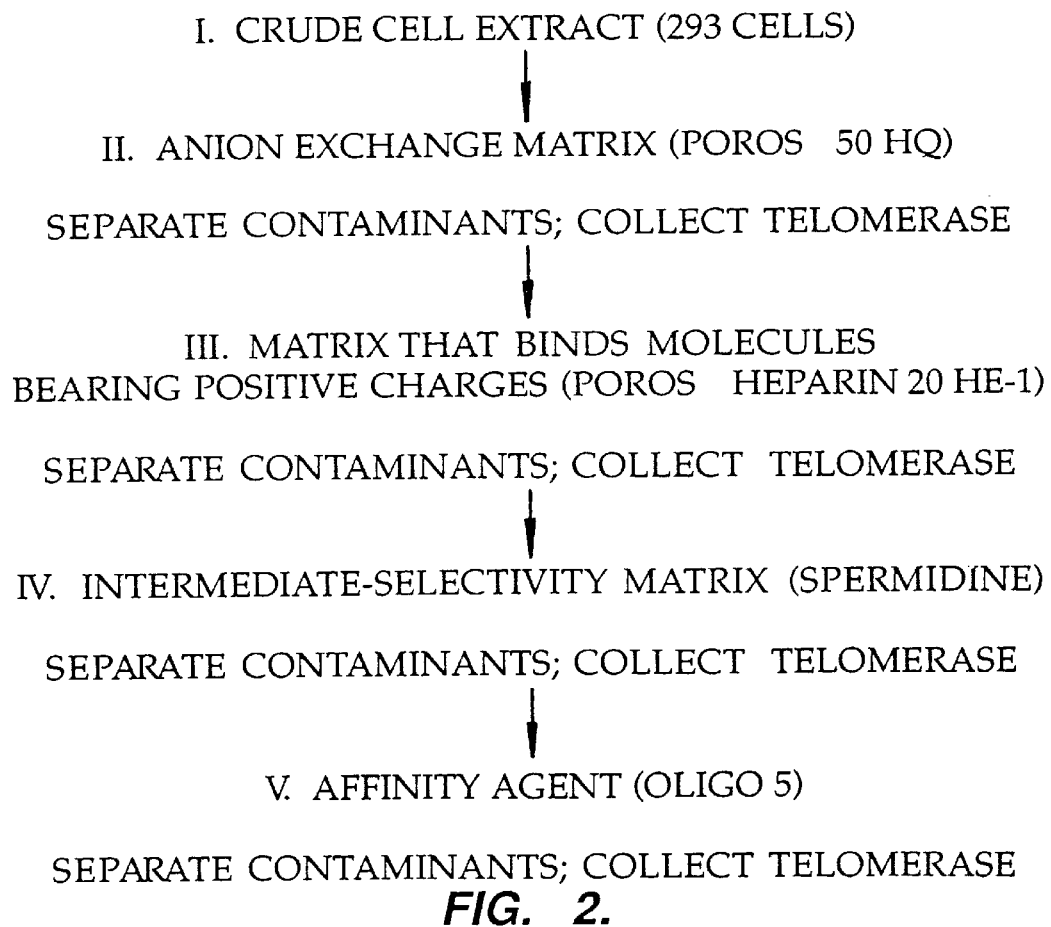
FIG. 2 depicts a five-step protocol for purifying telomerase.

Additional steps optionally can be included in the purification methods in order to produce telomerase preparations with higher relative purity. Telomerase can be further purified with an intermediate-selectivity resin (preferably a matrix containing spermidine) before affinity purification. See FIG. 2.

The specific purification steps used and their sequence is at the discretion of the practitioner. However, the following guidance is provided. In general, it is preferred to begin with steps having high capacity and relatively low selectivity, followed by steps having intermediate capacity and/or selectivity, followed by steps having low capacity and high selectivity. Matrices binding molecules bearing positive or negative charges have high capacity and are useful as early steps because telomerase is present in low quantities in cells and purification methods typically will begin with large amounts of crude cell extract. Among these resins, purification with anion exchange resins are preferred first, followed by purification with resins that bind molecules bearing positive charges. The order can be reversed.

Purification steps having intermediate selectivity and capacity are preferred after high capacity steps. These include matrices of intermediate selectivity and separation based on molecular size, shape or buoyant density. While purification with intermediate selectivity resins is preferred first, the intermediate purification steps need not be limited to any particular order or number. In the four-step purification procedure described above, the intermediate steps are not included.

Specific affinity matrices have relatively low capacity, but high selectivity, and are preferred later in the purification process when telomerase is present with fewer contaminating materials. This step can be a sole purification step and is most useful when telomerase has at least 40-fold increased relative purity.

2. Source of Telomerase

Purification of telomerase begins with an impure source composition, such as a nuclear extract or crude cell extract, preferably rich in telomerase activity. Single-celled organisms with no limits on the number of cell divisions, such as Tetrahymena or yeast, make telomerase and are good sources for cell extract in the preparation of telomerase from such organisms. However, in multicellular organisms, especially mammals, not all cells make telomerase. Therefore, sources have to be identified from the cell types available. In mammals, germ cells and tissue, cancer cells and tissue and immortalized cell lines are all sources of telomerase activity. In rodents and possibly other non-primate mammals, some normal somatic tissues, e.g., mouse liver, are sources of telomerase activity.

Immortalized cell lines are a particularly useful source of crude telomerase preparations because they can be cultured and harvested in large quantities, thereby providing cell extract for large-scale telomerase preparations. In particular, in the preparation of purified human telomerase, 293 cells are preferred. 293 cells are of human embryonic kidney origin that have been transformed with fragments of adenovirus type 5 DNA (Graham et al., 1977 *J. Gen. Virol.* 36:59–77). The cell line, which grows in monolayer cultures, was adapted to growth in suspension Stillman and Gluzman, (1985) *Mol. and Cell Bio.* 5:2051–2060). They are available from the American Type Culture Collection (ATCC) (Accession No. ATCC CRL 1573).

Crude nuclear extract can be prepared by separating nuclei from cytoplasm by a low-speed spin. A more detailed description is provided in Example VI, Section A.

The crude cell extract can be prepared in the typical manner. Generally, cells can be homogenized at about 4° C. in buffers at physiological pH. A more detailed protocol is provided in Example II. 293 cells are grown as suspension cultures in 8 liter spinner bottles in Joklik's - MEM, 5% newborn calf serum, 2 g/l $NaHCO_3$, 1% non-essential amino acids, 1% glutamine, 1% penicillin/streptomycin at 37°. The cultures are maintained at $0.6 \times 10^6$ cells/ml and double every 24 hours. One also may contract with a cell culture specialist to culture large batches of cells. Contractors include Analytical Biological Systems (Wilmington, Del.), Cellex (Minneapolis, Minn.) and Berlex (South San Francisco, Calif.).

Other cell types, particularly those that grow readily in suspension cultures (which facilitates large scale culturing), also are useful for purifying human telomerase. Candidates include cell lines of B or T cell lineage, such as Namalwa (Burkitt's lymphoma), Daudi (Burkitt's lymphoma), Jurkat (acute T cell leukemia) and HUT 78 (cutaneous T cell lymphoma) lines. Also, HeLa cells (cervical carcinoma) have telomerase activity. Extracts from HeLa cells are available from Computer Cell Culture Center (Mons, Belgium).

Nuclear extracts from 293 cells are a preferred source of telomerase. The crude cell extract from mammalian cells used in the methods of this invention can be whole cell extract or cytoplasmic extract.

The amount of impure preparation needed to purify telomerase depends, in part, upon the abundance of telomerase in the cell, the amount of telomerase lost at each step, and the ultimate degree of purification and amount desired. Example III describes the use of 128 liters of 293 cell suspension culture in a procedure that purified telomerase more than 3000-fold.

As purification advances, telomerase becomes both purer and more dilute. In this state, telomerase can be lost due to telomerase sticking to tubes, tubing, tips, etc. This loss can be minimized by the addition of detergent. In particular, the addition of up to about 0.1% Nonidet P-40 and about 1% Tween®-20 (non-ionic detergents) does not inhibit telomerase activity, and can be added to all chromatography buffers.

3. Matrices the Bind Molecules Bearing a Negative Charge

A preferred method for purifying telomerase from a crude cell extract involves contacting the telomerase with first and second matrices that bind molecules bearing negative charges, separating telomerase from other organic biomolecules that do not bind to the matrix and collecting the telomerase. Matrices binding molecules with a negative charge are useful in purifying telomerase because at pH between about 6 and about 9, the telomerase complex appears to have at least local negative charges. In a preferred embodiment of the invention the matrix is an anion exchange resin packed in a column. Anion exchange resins bind negatively charged molecules. One benefit of using anion exchange at this crude stage of preparation is the high binding capacity of these resins.

In isolating human telomerase, anion-exchange resins characterized by tertiary or quaternary amine functional groups provide the best results. POROS® 50 HQ (PerSeptive Biosystems, Cambridge, Mass.) and SOURCE 15Q (Pharmacia, Uppsala, Sweeden) are preferred anion exchange resins. Super Q-650M (TosoHaas, Montgomeryville, Pa.), DEAE Sepharose® CL-6B (Pharmacia, Uppsala, Sweden) and Mono Q® (Pharmacia, Uppsala, Sweden) are also useful. In eluting fractions from the anion exchange resin, salt step elution is preferred. Also, linear salt gradient elution may be used to elute telomerase preferably using gradient volumes of less than ten column volumes.

4. Matrices the Bind Molecules Bearing a Positive Charge

A preferred method of purifying telomerase involves, as a second step between two anion exchange purification steps, contacting the telomerase with a matrix that binds molecules bearing positive charges, separating telomerase from other organic biomolecules that do not bind to the column and collecting the telomerase. In a preferred embodiment the matrix comprises heparin. In particular, POROS® Heparin 20 HE-1 (PerSeptive Biosystems, Cambridge, Mass.) is useful as a matrix at this stage. Other useful matrices that bind molecules bearing positive charges include SP Sepharose® CL-6B and Resource™ S (Pharmacia, Uppsala, Sweden).

5. Intermediate Purification Steps

After the purification with high capacity matrices, and before affinity matrix purification, telomerase can be further purified through one or more intermediate purification steps.

In one intermediate purification step, the telomerase is contacted with hydroxylapatite, telomerase is separated from other organic biomolecules that do not bind to hydroxylapatite and the telomerase is collected. Hydroxylapatite is a crystalline form of calcium hydroxylphosphate which has the ability to bind proteins according to their basic or acidic character. Its basis of protein separation differs from that of simple ion exchange resins. Fractions may be eluted with buffers of different composition.

Figure 3:
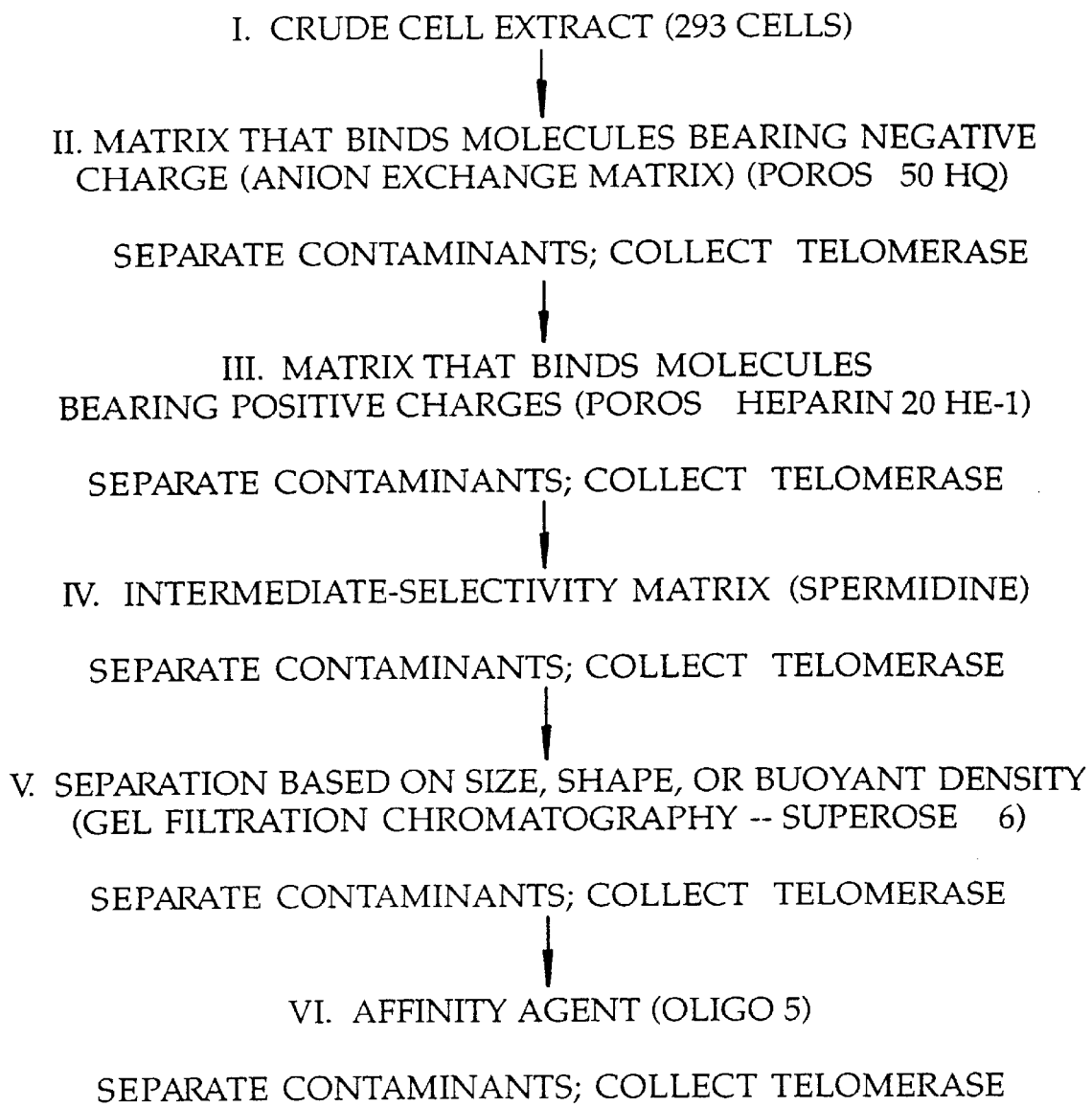
FIG. 3 depicts a first six-step protocol for purifying telomerase.

A preferred intermediate purification step involves contacting the telomerase with an intermediate-selectivity matrix; separating telomerase from other organic biomolecules that do not bind to the intermediate-selectivity matrix and collecting the telomerase. This step can be the fourth step of the five- or six-step purification schemes outlined in FIGS. 2 and 3. The main purpose of this step is to further purify the telomerase preparation before contacting it with an affinity agent. The types of matrices included at this step generally have lower binding capacities but can be more selective than ion exchange resins, thereby giving greater purification. They bind telomerase via interactions that are more complex than charge, alone, and are not as specific as, for example, antibodies. Binding characteristics can include, for example, combinations of electrostatic attraction, hydrophobic/hydrophilic attraction, affinity for particular components, such as nucleic acids or particular amino acids in the protein, affinity for chemical functional groups on molecules, and the variety of compounds known and used in protein purification for semi-specific separation of molecules. In particular, and without limitation, this invention contemplates the use of the following intermediate-selectivity matrices.

Matrices comprising a polyamine, such as spermidine or spermine are preferred in this step. These molecules contain primary and secondary amines amidst hydrocarbon chains. Both charge and hydrophobic interactions may be involved in binding telomerase.

Matrices comprising polynucleotides are useful in this step. In the case of human telomerase, polyguanylic acid retains telomerase activity. Without wishing to be bound by theory, these matrices are believed to be useful because telomerase is an enzyme that synthesizes DNA and contains an RNA moiety. Therefore, it is presumed to have domains which specifically bind polynucleotides.

Matrices comprising divalent metal ions are also useful in this step. Metals can be chelated on solid supports through molecules such as iminodiacetic acid or nitrilo-tri-acetic acid. Nickel is the most preferred metal and copper and zinc are also useful in purifying human telomerase. Without wishing to be limited by theory, metals are assumed to interact selectively with specific amino acid residues in proteins. Histidine residues typically are involved in such interactions. Depending on the immobilized metal, only those proteins with sufficient local densities of histidines will be retained by the column. Some interactions between metals and proteins can be so strong that the protein cannot be recovered. Thus, each metal must be tested empirically for its utility in purification of a given protein. The binding of telomerase, as well as the release of telomerase must be efficient.

Matrices comprising positively charged proteinaceous substances also are useful in this step of the purification method. As used herein, proteinaceous substances include amino acids, poly-amino acids, peptides and proteins. Two positively charged materials, poly-L-lysine, and histone, selectivity retained human telomerase.

Matrices comprising aminophenyl-boronic acid also retain human telomerase. While not wishing to be limited by theory, the affinity of proteins for boronic acid is complicated but essentially involves interaction between diol groups on proteins with the immobilized acid.

In one embodiment of the invention, the telomerase is contacted sequentially with at least 2, at least 3 or at least 4 intermediate-selectivity matrices. Since contaminating proteins are unlikely to behave like telomerase on matrices having different characteristics, the use of more than one matrix improves the level of purification at this step. Sequences producing higher yields and purifications can be determined empirically, and matrices having higher capacity are preferred earlier in the sequence. Some combinations of two matrices in the series are not preferred due to their similar modes of separation, for example, one divalent metal column followed by another, spermine followed by spermidine, poly-L-lysine followed by histone.

Another intermediate purification step in a method to purify telomerase involves separating the telomerase from other organic biomolecules according to molecular size, shape, or buoyant density and collecting the telomerase. This can be the fifth step in the six-step purification procedure outlined in FIG. 3. A preferred embodiment of this step involves fractionating the telomerase preparation by gel filtration chromatography. Sizing gel matrices that separate proteins in the size range of 200 kD to 2000 kD are most useful in human telomerase purification. Preferred matrices are HW65 (TosoHaas, Montgomeryville, Pa.), Superose® 6 (Pharmacia, Uppsala, Sweden) and, in particular, TSK-Gel*G5000PW$_{XL}$. Another embodiment of this step involves gradient centrifugation of the telomerase in gradients of different compositions that yield separation of the molecules in the preparation. Preferred gradients are composed of $Cs_2SO_4$ or of glycerol. Another embodiment of this step involves the use of gel electrophoresis, which separates molecules based on their charge, size and shape. The gel compositions may vary widely in this embodiment. A preferred gel is a native gel, composed of agarose, polyacrylamide, or both, that is run under physiological conditions of buffer strength and pH, which tend to preserve the native complex and activity of human telomerase.

6. Affinity Matrix

After the high capacity purification steps, and after the optional intermediate purification steps, telomerase is further purified by contacting the telomerase with an affinity agent having specific affinity for telomerase, separating telomerase from other organic biomolecules that do not bind to the affinity agent, and collecting telomerase from the affinity agent. Affinity agents in this step of the purification method are orders of magnitude more specific for binding telomerase over other organic biomolecules, than are the agents in the other steps of the method. Affinity agents having specific affinity for telomerase include, for example, oligonucleotides that are complementary to the RNA component of telomerase, oligonucleotides (RNA or DNA) having a primer sequence recognized by telomerase, antibodies that recognize epitopes of telomerase or telomerase associated proteins, and compounds that inhibit telomerase. A preferred affinity agent is Oligo 14ab, an oligonucleotide whose sequence is given in Table 2. Anti-nucleolin antibody and anti-TMG antibody also are useful.

Oligonucleotides comprising a nucleotide sequence complementary to a sequence of the RNA component of telomerase (e.g., an "antisense sequence") are useful as affinity agents. In one embodiment, the oligonucleotide is attached to a retrievable label, e.g., biotin. "Peptide nucleic acids," polymers having an amide backbone and attached bases, are also useful as affinity agents. The label can be on one or both ends. After contacting the telomerase with the labeled affinity agent, the affinity agent is contacted with a binding agent that binds to the retrievable label, e.g., streptavidin or derivative agent. Preferably, the binding agent is attached to a matrix. Then, molecules that have not bound to the retrievable affinity agent, and therefore are not bound to the binding agent, are separated or removed from the mixture. By releasing telomerase from the affinity agent, telomerase is purified.

The use of retrievable labels is well known in the art. The retrievable label and binding agent can be any sort of ligand and ligand partner. In a preferred embodiment, the retrievable label is biotin and the binding agent is ImmunoPure® NeutrAvidin (Pierce, Rockford, Ill., catalog number 53157). In one embodiment, the retrievable label is an antigen and the binding agent is an antibody that binds the antigen.

A general experimental procedure for testing nucleic acid affinity approaches is as follows: (i) biotin-labeled oligonucleotides are mixed under various conditions with partially purified telomerase; (ii) beads with attached NeutrAvidin are added to the mixture; (iii) beads are separated from the mixture (telomerase that has stuck to the oligonucleotide has also stuck to the beads, so activity is depleted from the mixture); (iv) beads are washed to remove bound material (telomerase comes off the beads, and activity is recovered).

Oligonucleotides complementary to a sequence of the RNA component of human telomerase were tested for their ability as affinity agents. Oligonucleotides useful in the methods of the invention are given in Table 1. Each of the antisense oligos was tested in parallel with a control non-specific oligo. Depletion refers to the retention of telomerase by the oligo; recovery refers to the subsequent release of telomerase from the oligo.

Oligo 14ab is the preferred oligo for affinity purification. Oligo 14ab hybridizes to a region of hTR that is accessible in the holoenzyme.

Oligo 5 also is a good oligonucleotide for affinity purification. While not wishing to be bound by theory, Oligo 5 is a strong non-processive primer, so it may not be acting as an antisense ligand; it may be acting as a primer ligand. Using Oligo 5 and eluting with varying salt concentrations, telomerase activity has been recovered in a set of fractions containing low levels of detectable protein (10 μg/ml), making this a highly enriched preparation of telomerase. The yield of telomerase activity was 29%. (See Example III).

TABLE 1

Oligonucleotides complementary (antisense) to human telomerase RNA.

| Oligo Name | Size (nt) | Description | Performance |
| --- | --- | --- | --- |
| anti-P | 31 | Direct antisense hTR, covers template | Good depletion, inhibits activity. |
| P3 | 22 | Antisense hTR plus a primer terminus | Good depletion, recovery of telomerase. |
| Oligo 5 | 30 | Antisense hTR | Good depletion, recovery of telomerase. |
| Oligo 13 | 30 | Antisense hTR | Some depletion. |
| Oligo 14 | 30 | Antisense hTR | Good depletion. |
| Oligo 14ab | 20 | Antisense hTR to accessible region | Good depletion, recovery of telomerase. |

TABLE 2

| | Oligonucleotide Sequences |
| --- | --- |
| anti-P | (SEQ ID NO:2):<br>5' BIOTIN - gcctacgccc ttctcagtta gggttagaca - a - 3' BIOTIN |
| P3 | (SEQ ID NO:3):<br>5' - BIOTIN - cgcccttctc agttaggggtt ag - 3' |
| Oligo 5 | (SEQ ID NO:4):<br>5' - BIOTIN gccgagtcct gggtgcacgt cccatagct c - 3' |
| Oligo 13 | (SEQ ID NO:5):<br>5' - BIOTIN - gaacgggcca gcagctgaca tttttttgttt - 3' |
| Oligo 14 | (SEQ ID NO:6):<br>5' - BIOTIN gctctagaat gaacggtgga aggcggcagg - 3' |
| Oligo 14ab | (SEQ ID NO:14):<br>5' - BIOTIN - cgttcctctt cctgcggcct - 3' |

In another embodiment of this step, the affinity agent is an oligonucleotide having a primer sequence recognized by telomerase. The oligonucleotide is contacted with the telomerase and dideoxy nucleotides under conditions for a primer elongation reaction. This results in chain termination of DNA synthesis by telomerase. Under these conditions, telomerase may lock on the chain terminated primer. The primer and the telomerase attached to it is isolated. The oligonucleotide preferably includes sequences that have been found to be efficient primers in the primer elongation assay. This includes the sequence synthesized by telomerase as well as non-telomeric sequence primers such as M2/TS. For example, human telomerase synthesizes telomeric DNA sequences (TTAGGG), onto the 3' end of single-stranded DNA (and RNA) primers. Thus, an oligonucleotide for isolating human telomerase can have the sequence (TTAGGG)₃ (SEQ ID NO:8). Sequences synthesized by other telomerases are identified in, for example, E. H. Blackburn, (1991) *TIBS* 16:378–381.

The above embodiment was tested using biotinylated oligonucleotides as primers, which were subsequently retrieved with NeutrAvidin beads. Controls were non-primer oligos, such as (CCCTAA)₃ (SEQ ID NO:9). Preferred oligonucleotides for affinity purification in this embodiment are M2/TS and (TTAGGG)₃ (SEQ ID NO:8). The sequence of useful oligonucleotides is given in Table 3.

TABLE 3

| Oligo Name | Size (nt) | Description | Performance |
| --- | --- | --- | --- |
| (TTAGGG)₃<br>(SEQ ID NO:8) | 18 | Telomeric primer | Good depletion, recovery of telomerase |

TABLE 3-continued

| Oligo Name | Size (nt) | Description | Performance |
|---|---|---|---|
| M2/TS | 18 | Non-telomeric primer | Good depletion, recovery of telomerase |
| Biotin-SS-(TTAGGG)₃ (SEQ ID NO:15) | 18 | Cleavable telomeric primer | Slight depletion, some recovery |

Oligonucleotide Sequences:

M2/TS (SEQ ID NO:10)
5' - BIOTIN - aatccgtcga gcagagtt - 3'

With the various primer oligos used, the efficiency of depletion correlated with the strength of the primer in a telomerase primer elongation assay. The M2/TS primer showed the best ability to deplete and retain the activity. Some telomerase activity was eluted with DTT from a biotinyl-SS-(TTAGGG)₃ (SEQ ID NO:15) primer depletion (the DTT breaks the disulfide linkage in the primer, releasing it from the beads). The yield was only 1–5%, but the purity was likely high (protein concentration was below detection by standard protein assay).

In another embodiment of this step, the affinity agent is an antibody that specifically recognizes an epitope of telomerase. Antibodies useful as affinity reagents include antibodies against nucleolin and antibodies against the trimethylguanosine ("TMG") cap structure found on various small nuclear RNAs. One source of antibodies that may recognize human telomerase are antibodies that recognize the telomerase of other organisms. Those antibodies may cross react with human telomerase due to homology. Primary sequences of the 80 kD and 95 kD protein subunits of Tetrahymena telomerase have been analyzed for regions of antigenicity and surface probability. From this analysis, two peptides for the 80 kD and one for the 95 kD have been designed. These peptides have the following sequences:

GP 80A:
CRKKTMFRYLS VTNKQKWDQT KKKRKEN (SEQ ID NO:11)—80 kD protein

GP 80B:
CHISEPKERV YKILGKKYPK TEEE (SEQ ID NO: 12)—80 kD protein

GP 95A:
DNNLCILALL RFLLSLERFN IL (SEQ ID NO:13)—95 kD protein

These peptides were used to raise antibodies. In choosing Tetrahymena protein sequences for this purpose, selecting for surface probability is very important because antibodies against external features of telomerase are most likely to immunoprecipitate the telomerase activity from other organisms. In another embodiment, antibodies are raised against fusion proteins bearing a portion of a telomerase polypeptide component and made in, e.g., an E. coli expression system. In another embodiment, the antibodies are from humans afflicted with autoimmune disease. In another embodiment, antibodies are identified from among antibodies that recognize epitopes on enzymes that are functionally related to telomerase, e.g. DNA replication enzymes and reverse transcriptases. In another embodiment, the antibodies are raised against peptides from the sequence of human telomerase proteins.

In another embodiment of this step, the affinity agent is an inhibitor of telomerase activity that binds to telomerase. Telomerase inhibitors and methods of assaying for them are described in Prowse et al., U.S. patent application Ser. No. 08/288,501, filed Aug. 10, 1994. When attached to a retrievable label, these compounds provide a hook by which to isolate telomerase.

After the molecules that do not bind to the affinity agent are removed, the bound telomerase is released from it. When the affinity agent is an oligonucleotide, extremes of ionic strength (e.g., high (about 500 mM NaCl) or low (zero) salt), exposure to high concentrations of nucleotides, and the use of cleavable oligos (disulfide oligos shown in Table 3) have been tried in efforts to release the bound enzyme. Washing an Oligo 5 column with salt solutions of increasing ionic strength releases telomerase.

When the M2/TS affinity column matrix with bound telomerase was boiled, and the released material was analyzed on a silver stained SDS gel, there were very few bands apparent (less than 10). While in this experiment telomerase proteins were likely below the limit of detection, this result indicated that very few other proteins were bound to the affinity matrix. Thus the specificity of this affinity depletion was high.

Adding a second affinity step significantly increases the purity of telomerase. For example, if an oligo 14ab affinity step is followed by affinity purification with anti-nucleolin or anti-TMG, telomerase is purified to about 500,000-fold.

7. Purification based on Molecular Size, Shape or Buoyant Density

In a preferred method of the invention, the affinity purification step is followed by a step involving separating telomerase from other organic biomolecules according to molecular size, shape, or buoyant density. Matrices that separate molecules according to size, such as gel exclusion chromatography, are especially useful at this stage. A preferred matrix is a TosoHaas TSK-Gel*G5000PW$_{XL}$ sizing column. Telomerase in these fractions was purified to greater than 60,000-fold relative purity. Fractions containing telomerase activity at this stage were separated by SDS-PAGE. They contained about 50 visible protein bands. Isolating the bands from the gel results in a substantially pure protein.

Purified telomerase is useful to produce antibodies against the protein. It also is useful as a control in assays for detecting telomerase in a sample. Recombinant telomerase, produced in cells, is useful for immortalizing those cells. Immortalization is useful in the preparation of self-replicating cell lines.

III. TELOMERASE RELATED PROTEINS

Figure 4:
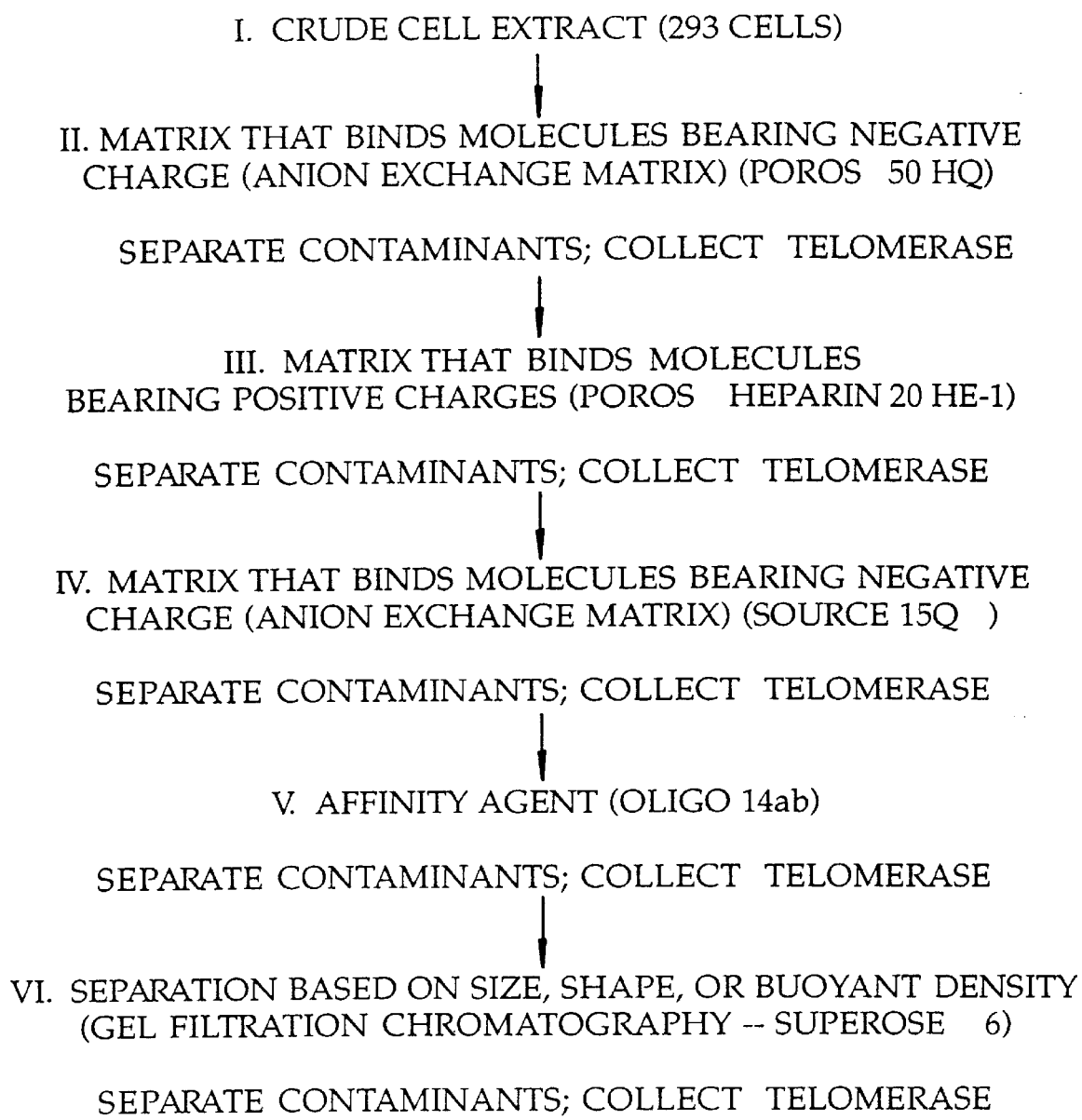
FIG. 4 depicts a second six-step protocol for purifying telomerase.

After purifying telomerase using the protocol presented in FIG. 4, the proteins in fractions containing telomerase activity were examined by gel electrophoresis. Two polypeptides were identified in the purified fractions that co-purified with telomerase activity and that were found in approximate stoichiometric amounts with the RNA component of telomerase. One protein, designated b120, had an apparent molecular mass of 120 kD on SDS-PAGE. Another protein, designated y105, had an apparent molecular mass of 105 kD on SDS-PAGE.

The proteins were further characterized. The proteins were fragmented with protease and the amino acid sequence of the fragments were determined by nano-electrospray mass spectrometry. This method is described in M. Wilm et al., (1996) "Femtomole sequencing of proteins from polyacrylamide gels by nano-electrospray mass spectrometry," Nature 379:466469. Amino acid sequences from peptides derived from b120 and y105 were compared with known amino acid sequences in the sequence database Genbank.

Peptide fragments of b120 were identified as having amino acid sequences identical to sequences of elongation factor 2 homolog ("EF2H"). See N. Nomura et al., "Prediction of the coding sequences of unidentified human genes. I. The coding sequences of 40 new genes (KIAA0001–KIAA0040) deduced by analysis of randomly sampled cDNA clones from human immature myeloid cell line KG-1," (1994) *DNA Res.* (JAPAN) 1:27–35. GENBANK accession # D21163. EF2H is a cDNA randomly isolated from a cDNA library whose sequence is homologous to elongation factor 2. Its function has not previously been identified. Elongation factor 2 functions in the translocation of mRNA in the ribosome. Polypeptide b120 is referred to herein as elongation factor 2 homolog.

Peptide fragments of y105 were identified as having amino acid sequences identical to sequences of nucleolin. Nucleolin is a nucleolar resident protein understood to function in ribosome assembly. See, e.g., M. Srivastava et al. (1989) "Cloning and sequencing of the human nucleolin cDNA," *FEBS Letters* 250:99–105 and M. Srivastava et al. (1990) "Genomic organization and chromosomal localization of the human nucleolin gene," *J. Biol. Chem.*, 265:14922–931. GENBANK accession no. M60858 J05584. Polypeptide y105 is referred to herein as "nucleolin."

IV. USES OF TELOMERASE RELATED PROTEINS

Telomerase activity can be immunoprecipitated from nuclear fractions with anti-nucleolin antibodies. Because it binds telomerase, nucleolin is a telomerase associated protein. Nucleolin functions in vivo as a telomerase activity factor.

Accordingly, this invention provides methods of isolating telomerase in which telomerase is contacted with nucleolin and the telomerase-nucleolin complex is isolated from other contaminating molecules. In one embodiment, an affinity matrix comprising nucleolin is contacted with telomerase, and contaminating molecules are washed from the matrix. In another embodiment, nucleolin is first derivatized with one of a pair of ligands, such as GST/glutathione or biotin/streptavidin and then contacted with telomerase to form a complex. The complex is captured on an affinity matrix derivatized with the binding partner. In another embodiment, telomerase associated with nucleolin (either naturally, or by prior contact with telomerase) is isolated from a mixture using an affinity matrix comprising anti-nucleolin antibodies.

Nucleolin appears to function in the process of telomerase assembly and telomerase-mediated extension of the telomeres of chromosomes in vivo. This invention provides methods of making natural or recombinant telomerase that involve expressing recombinant nucleolin in a cell that expresses other components of telomerase. Such cells include those that express recombinant components of telomerase.

This invention provides methods of screening compounds to identify agents that alter the association of telomerase-associated proteins, such as nucleolin or EF2H, with telomerase. The methods generally involve contacting a compound with the telomerase-associated protein and/or with telomerase, and determining whether the association between the telomerase-associated protein and telomerase is altered by the presence of the compound. An alteration indicates that the agent alters telomerase binding to the associated protein. Binding of an associated protein to telomerase can be determined by a variety of means, including by the methods described determining whether telomerase can be co-isolated or co-detected with the associated protein. These methods are useful in identifying agents that can modulate telomerase assembly or activity in vivo.

Nucleolin and EF2H are believed to function as telomerase activity factors in vivo. This invention provides methods of screening compounds to identify agents that alter telomerase activity or function. The methods involve expressing a recombinant telomerase activity factor, such as nucleolin or EF2H, in a cell that produces telomerase, contacting the cell with the agent, and determining whether telomerase activity or function is altered, e.g., by measuring telomerase activity or telomere length. In another method, the compound is contacted with the telomerase activity factor and/or telomerase in vitro, and the ability of the telomerase activity factor to alter telomere activity is determined and compared with its ability to alter telomerase activity without the presence of the compound.

This invention also provides methods for inhibiting telomerase assembly or telomerase activity in vivo by inhibiting the activity of a telomerase activity factor, such as nucleolin or EF2H. In one embodiment, the methods involve inhibiting telomerase assembly or activity by providing the cell with an antisense molecule directed against DNA or RNA encoding the telomerase activity factor. In another embodiment, the methods involve expressing mutant, non-functional versions of a telomerase activity factor to act as a decoy against the natural activity of these proteins. Such mutants can be, for example, fragments of the native protein, mutants comprising several non-conservative amino acid substitutions, additions, deletions and the like.

Both nucleolin and EF2H are useful for identifying other telomerase-related proteins that bind nucleolin or EF2H, as can be performed, for example, using a two hybrid screen. See, e.g., Chien et al. (1991) *Proc. Natl. Acad. Sci. (USA)* 88:9578. This screen identifies protein-protein interactions in vivo through reconstitution of a transcriptional activator, the yeast Gal4 transcription protein. See Fields and Song (1989) *Nature* 340:245. The method is based on the properties of the yeast Gal4 protein, which consists of separable domains responsible for DNA-binding and transcriptional activation. Polynucleotides, usually expression vectors, encoding two hybrid proteins are constructed. One polynucleotide comprises the yeast Gal4 DNA-binding domain fused to a polypeptide sequence of a known protein (e.g., nucleolin or EF2H). The other polynucleotide comprises the Gal4 activation domain fused to a polypeptide sequence of a second protein to be tested (e.g., cDNA from a library). The constructs are introduced into a yeast host cell. Upon expression, intermolecular binding between the attached moieties of the two fusion proteins can reconstitute the Gal4 DNA-binding domain with the Gal4 activation domain. This leads to the transcriptional activation of a reporter gene (e.g., lacZ, HIS3) operably linked to a Gal4 binding site. Variations of two-hybrid systems have been used to study the in vivo activity of a proteolytic enzyme. See Dasmahapatra et al. (1992) *Proc. Natl. Acad. Sci. (USA)* 89:4159. Alternatively, an *E. coli*/BCCP interactive screening system can be used to identify interacting protein sequences (i.e., protein sequences which heterodimerize or form higher order heteromultimers). See Germino et al. (1993) *Proc. Natl. Acad. Sci. (U.S.A.)* 90:933; Guarente (1993) *Proc. Natl. Acad. Sci. (U.S.A.)* 90:1639. Once such cDNAs encoding such interacting polypeptides are identified, they may be used for screening a bank of compounds (e.g., small molecule libraries) to identify agents which inhibit the binding interaction.

V. POLYNUCLEOTIDES ENCODING TELOMERASE RELATED PROTEINS

This invention also provides polynucleotides having nucleotide sequences encoding telomerase related proteins, including protein components of telomerase, telomerase associated proteins and telomerase activity factors. Nucleotide sequences that encode telomerase related proteins are inherent from the amino acid sequence of these polypeptides and the genetic code. These nucleotide sequences can be used in the preparation of recombinant polynucleotides used for expressing telomerase related proteins in various expression systems.

In one embodiment, the polynucleotide comprises the sequence of cDNA or genomic DNA encoding a protein component of telomerase. Such polynucleotides are obtained, for example, in the following manner. The full or partial amino acid sequences of the protein component of telomerase are used to create degenerate sets of polynucleotide probes or primers that encode the amino acid sequences. As is well known to one skilled in the art, it is preferable to select amino acid sequences containing amino acids encoded by as few codons as possible (preferably unique codons) in order to decrease the number of possible polynucleotides that encode the sequence. These probes or primers are then used to probe or amplify polynucleotide sequences from cDNA libraries or genomic DNA. Naturally occurring polynucleotide sequences encoding telomerase associated proteins are identified by sequencing positive clones or amplified sequences.

In another aspect, this invention provides polynucleotide probes and primers of at least 7 nucleotides that specifically hybridize to a naturally occurring sequence encoding a telomerase associated protein or its complement. Probes and primers are useful for detecting polynucleotides encoding telomerase protein components. The detection of telomerase protein component mRNA is useful in detecting cancer in a cell because most cancerous cells express telomerase.

In another aspect, this invention provides methods for detecting a polynucleotide encoding a protein component of telomerase in a sample, comprising the steps of (a) contacting the sample with a polynucleotide probe or primer comprising a sequence of at least 7 nucleotides that specifically hybridizes to a nucleotide sequence selected from the nucleotide sequence of the telomerase protein component and (b) detecting whether the polynucleotide has specifically hybridized to the telomerase protein component polynucleotide. Specific hybridization provides a detection of the telomerase protein component in the sample.

In another aspect this invention provides methods for inhibiting telomerase expression in a cell comprising providing the cell with an inhibitory polynucleotide that specifically binds to a telomerase protein component polynucleotide, e.g., mRNA. The inhibitory polynucleotide can be an antisense molecule, a ribozyme, a sense molecule, or a decoy that encodes an inactive decoy telomerase analog.

Recombinant polynucleotides that include expression control expression control sequences operatively linked to a nucleotide sequence encoding a protein component of telomerase are useful in making large amounts of recombinant telomerase. In one embodiment, the method involves providing the cell with an expression apparatus for recombinant expression of the related proteins of telomerase and the RNA component of telomerase. Alternatively, a cell that already expresses one or more of the components of the ribonucleoprotein can be complemented with an expression apparatus to express the other components.

VI. METHODS OF ELICITING AN IMMUNE RESPONSE AGAINST TELOMERASE

Purified telomerase, telomerase associated proteins or natural or synthetic peptides derived from them also are useful for inducing an immune response in animals. Accordingly, this invention provides polynucleotide and polypeptide vaccines for eliciting a humoral or cell-mediated immune response against telomerase, telomerase associated proteins or cells expressing it. This invention also provides methods of producing antibodies that recognize telomerase or telomerase associated proteins, both polyclonal and monoclonal. Antibodies that specifically recognize telomerase or telomerase associated proteins are useful affinity agents in methods for isolating those proteins, or as controls in immunoassays for them. The methods involve immunizing an animal with purified telomerase, a telomerase associated protein or a fragment of any of them.

Antibodies that specifically recognize telomerase or a telomerase associated protein also are useful for detecting the presence of these proteins in a sample, such as a cell or tissue. Because telomerase is present in most cancers, the identification of telomerase aids in the diagnosis of cancer or pre-cancerous states. Detecting the presence of telomerase with antibodies is inexpensive and offers speed and ease. Purified telomerase or immunogenic fragments of it also are useful in vaccines to immunize a subject.

A polypeptide or polynucleotide vaccine for eliciting an immune response against telomerase comprises an immunogenic telomerase polypeptide analog or a polynucleotide encoding the analog. In one embodiment, the immunogenic analog bears an MHC Class I or MHC Class II binding motif. The use of fragments of self proteins as immunogens is known in the art and is described for Cytotoxic T Lymphocyte priming in International publication WO 94/03205. Vaccines comprising these materials are useful in treating diseases associated with the over-expression of telomerase, such as cancer.

EXAMPLES

I. TELOMERASE ASSAY PROTOCOLS

A. Primer Elongation Assay a) Assay

The primer elongation assay described in this example is the standard for determining specific activity for the purposes of determining relative purity of a telomerase preparation.

The 40 $\mu$l telomerase reaction should have a final concentration of:

1. 1× Telomerase Buffer (see below)
2. 1 mM $MgCl_2$
3. 2 mM DATP, 2 mM dTTP, 8 $\mu$M dGTP
4. 1 $\mu$M or 0.25 $\mu$g/reaction of oligo primer M2/TS
5. 20 $\mu$Ci/reaction of ($\alpha^{32}$P-dGTP (0.624 $\mu$M dGTP, spec. activity 800 Ci/mmole; NEN)

1. To start the reaction, combine 20 $\mu$l of the 2× reaction mix with an equal volume (20 $\mu$l) of enzyme extract. For RNase control, add 1 $\mu$l of RNase A at 5 mg/ml to buffer mix just before adding extract. (Final concentration of RNase is 125 $\mu$g/ml)

2. Incubate at 30° C. for 90 min (total volume=40 µl).

3. To stop reaction, add 50 µl of TE stop solution (10 mM Tris pH 7.5 and 20 mM EDTA) containing 100 µg/ml of RNase A (Stock=10 mg/ml; 100× dilution). Final concentration is 55 µg/ml}.

4. Incubate at 37° C. for 15 min (total volume=90 µl).

5. To eliminate proteins add 50 µl of 10 mM Tris pH 7.5, 0.5% SDS, and 300 µg/ml proteinase K. (Final concentration of PK is 107 µg/ml, and 0.18% SDS; make up fresh each time).

| For 1 ml: | 10 µl 1.0M Tris |
|---|---|
| | 25 µl 20% SDS |
| | 30 µl PK (10 mg/ml) |
| | 0.935 ml Depc water |

6. Incubate at 37° C. for 15 min (total volume=140 µl).

7. Extract with an equal volume (140 µl) of PCIA (phenol:chloroform:isoamyl alcohol (25:24:1)). Transfer aqueous phase to fresh tube.

8. Precipitate DNA by adding 40 µl of 2.5 M $NH_4OAC$ (good for precipitating small oligos) containing 100 µg/ml of tRNA (10 mg/ml stock; 100× dilution. 30 µg carrier/tube) and 2–3 volumes (500 µl) of cold absolute ethanol.

9. Let sit −20° C. for 30 min or overnight.

10. Spin in microcentrifuge for 15 min at room temperature.

11. Discard supernatant and dry pellet in a speed-vac, or air dry overnight. Optional; rinse pellet with 50 µl of cold ethanol.

12. Resuspend pellet in 3 µl of sequencing loading dye (99.9% formamide, 0.05% xylene cyanol, and 0.05% bromphenol blue).

13. Boil for one minute, and chill on ice.

14. Load samples onto an 8% acrylamide/7 M urea sequencing gel and run at 1500 V (50 W). (until BPB is about ⅔ to ¾ of the way down).

15. Transfer gel onto Whatman filter paper and dry at 80° C. for 35 minutes, and cool for 15 min before removing gel from dryer.

16. Expose gel to phosphoimager screen (Molecular Dynamics). Typical exposures are between 6 and 24 hours.

b) Human Telomerase Assay Solutions 1. 10× Telomerase Buffer

| Component amt/10 ml | (stock) | (10×) | (1×) | for 10 ml of 10× |
|---|---|---|---|---|
| 1. Tris.Cl pH 7.5 | 1 | 500 mM | 50 mM | 5 ml |
| 2. Spermidine · 3HCl | 1M | 10 mM | 1 mM | 100 µl |
| 3. BME* | 14.3M | 50 mM | 5 mM | 35 µl |
| 4. $MgCl_2$ | 1M | 10 mM | 1 mM | 100 µl |
| 5. K-OAc | 5M | 500 mM | 50 mM | 1 ml |
| 6. EGTA | 0.5M | 10 mM | 1 mM | 200 µl |
| | | | | DEPC |
| | | | | 3.565 ml |

*Alternatively, make (−)BME, aliquot 1 ml. Add 3.5 µl BME to give 10× before use.

2. Stop Solution

| Component | (stock) | (final) | amt/10 ml |
|---|---|---|---|
| 1. Tris.Cl pH 7.5 | 1M | 10 mM | 100 µl |
| 2. EDTA | 200 mM | 20 mM | 1 ml |

3. Cold dNTP's

Use e.g., Pharmacia (Uppsala, Sweden), 100 mM stocks.

Combine 10 µl of DATP and 10 µl of dTTP in one tube and store at −20° C. or −70° C.

Do not use the same tube more than 3× since dNTP's are unstable with repeated freeze/thaws. If making a dilution, use 10 mM Tris.Cl pH 7.5 (do not use water since the acidic pH will destroy the nucleotide).

4. Oligo Primer

Prepare sequence on synthesizer or buy commercially (e.g., Operon).

Gel (10% acrylamide/7M Urea) purify the crude oligo, and concentrate using a C-18 column. Dry in a speed-vac, and resuspend pellet in 10 mM Tris.Cl pH 7.5. A 30% to 45% yield is usually obtained. About half of the oligo is lost during gel purification, and 5% to 30% is lost from the column. Preferably purify 300 to 600 µg and resuspend final pellet in 40 µl of buffer. Determine the concentration by reading the absorbance at 280 nm. Assume for an oligo that 1 OD=30 µg/ml.

B. Telomerase Activity Dot Blot Assay

1. Combine components of Assay Mix:

| | Vol | Stock | Final Conc (in 40 µl) |
|---|---|---|---|
| | 4.0 µl | 10X HTB | 1X |
| | 0.4 µl | 100 mM dATP | 1 mM |
| | 0.4 µl | 100 mM dGTP | 1 mM |
| | 0.4 µl | 100 mM dTTP | 1 mM |
| | 1.0 µl | 0.25 µg/ml Oligo M2/TS | 1 µM |
| | 13.8 µl | depc $H_2O$ | |
| $V_t=$ | 20.0 µl | | |

2. Add 20 µl of test extract, mix and incubate at 30° C. for 90 min.

3. Add 160 µl of 0.5 M NaOH, 12.5 mM EDTA (Final Conc=0.4 M, 10 mM), mix, and let sit at room temp for 5 min.

4. Transfer samples to a Silent Monitor, Biodyne® B (0.45 µM) 96-well plate, then place plate on vacuum manifold to filter sample.

5. Turn off vacuum and add 200 µl 0.4 M NaOH to wells, and apply vacuum until filter is quite dry.

6. Peel off membrane filter, rinse in 2× SSC (to neutralize NaOH), and place in 50 ml of prewarmed prehybridization mix (6× SSC, 1× Denhardt's, 20 mM NaPhos pH 7.2, 0.4% SDS, depc $H_2O$) for 1 hour at 65° C.

7. Make riboprobe using Stratagene RNA transcription kit (HindIII-digested pBLRep4 DNA template, T3 RNA polymerase). To stop the reaction, add 1 µl of RNase-free DNase and incubate at 37° C. for 15 min, PCIA extract (equal vol), add 1/10 vol of 3 M NaOAc and 2.5 vol of ethanol to precipitate the RNA probe. Centrifuge 10 minutes and dissolve RNA in 100 µl TE in depc (diethylpyrocarbonate) $H_2O$.

8. Hybridize blot by adding 50 µl of probe per filter and incubate overnight at 65° C.

9. Next day, heat wash solution (1× SSC, 0.1% SDS) to 65° C. and transfer filter to wash solution. Rinse quickly, transfer filter to fresh solution, discard wash into radioactive waste and repeat. Wash four more times for 15 minutes each at 65° C.

10. Remove filter from wash solution and drain off excess liquid. Seal in bag and expose to PI screen for 1 hour. Scan screen and quantitate using grid.

C. RT-PCR Assay a. RNA Preparation:

1. RNA is extracted from column fraction: 300 μl/reaction.

2. Prepare 1 ml 10% SDS, 100 mM EDTA solution freshly before use: 200 μl stock 500 mM EDTA, 800 μl stock 10% SDS up to 1 ml.

3. In each reaction, add 30 μl of above SDS, EDTA buffer and 5 μl of stock Proteinase K (10 μg/μl) to each reaction, so the final concentration is: 1% SDS, 10 mM EDTA, 50 μg proteinase K.

4. Incubate at 37° C. for 10 min.

5. Phenol:Chloroform extract twice (be careful not to take the white interphase material).

6. To the final supernatant, 30 μl of 3 M sodium acetate is added, and the nucleic acids are precipitated by addition of 900 μl 100% ethanol and incubation at −70° C. or dry ice for 30 min.

7. To spin down the precipitate, microcentrifuge at full speed for 15 minutes, draw out all liquid, and use 200 μl 85% ethanol to rinse the pellet, then use speedy-vac to dry the pellet.

8. Resuspend the pellet in 30 μl Depc water. Take 1 μl resuspension into 100 μ; Depc water, and read $OD_{260\ nm}$. Use OD260=40 μg/ml to calculate RNA concentration.

b. First Strand cDNA Synthesis.

1. Take 0.1 to 1 μg RNA made form each telomerase fractions, and is mixed with 40 to 80 ng random hexamer, up to 10 μl. Random hexamer, from e.g., Pharmacia pd(N)6, total 50 OD unit powder/vial. Use 90 OD unit/ml=2.97 mg/ml, which is 1 OD unit=33 μg.

2. Denature at 95° C. for 10 min, chilled on ice, and spin down the vapor on the top of Eppendorf tube.

3. Prepare the reaction mixture:

|  | 1 Rx | 13 Rx |
| --- | --- | --- |
| 5x 1st stand sys. buffer (BRL): | 4 μl | 52 μl |
| 0.1M DTT (BRL): | 2 μl | 26 μl |
| 10 mM dNTP (BRL): | 1 μl | 13 μl |
| RNAguard ® (Pharmacia): | 1 μl | 13 μl |
| Depc $H_2O$: | 1 μl | 13 μl |
| TOTAL: | 9 μl | 117 μl |

Add 9 μl/each reaction, and incubation at 42° C. water bath.

4. After 1–2 min incubation, 1 μl Superscript II RTase (BRL) is added to the mixture, and incubated for 60 min at 42° C.

5. Stop the reaction by heating the tube for 10 min at 95–98° C. Chill on ice, and spin down the vapor.

c. PCR Amplification of cDNA with Specific Primer Set
1. PCR reaction buffer:

|  | 1 Rx | 13 Rx |
| --- | --- | --- |
| primer 1: | 1 μl | 13 μl |
| primer 2: | 1 μl | 13 μl |
| 2.5 mM dNTP: | 2.5 μl | 32.5 μl |
| 5 μ/μl Taq polymerase (BM): | 0.4 μl | 5.2 μl |
| 5 mg/ml T4 gene 32 protein (BM): | 0.04 μl | 0.52 μl |
| 10x TCR buffer (BM): | 2 μl | 26 μl |
| 10 μCi/μl α-32P dATP | 0.5 μl | 6.5 μl |
| Depc $H_2O$: | 10.56 μl | 137.28 μl |
| TOTAL: | 18 μl | 234 μl |

In 2 μl of first strand cDNA, add 18 μl of above PCR reaction buffer. One drop of mineral oil is then added to each PCR tube.

2. Set up condition of PCR amplification for hTR clone: 94° C. for 34 sec, 72° C. for 45 sec, 72° C. for 1.5 min, 20 cycles.

3. After PCR, 5 μl of the product is mixed with 10x DNA sequencing loading dye, and loaded on 6% native polyacrylamide gel (do not need to pre-run the gel). Run at 250 volts for 90 min. Dry the gel and PI exposure. It will be clear that one can substitute known equivalents in the above protocols.

D. Telomerase RNA Detection By Northern Analysis

1. Gel parameters 20 cm long gel 1 mm comb with 16 wells

5% Acrylamide gel/7 M Urea in 1x TBE

Run the gel O/N at 125 V for about 12 hr. (the BPB and XC will have run off the gel). U2 will be near the bottom, and hTR will be about ¼ of the way down into the gel.

hTR runs at about 700 nt with respect to DNA markers when using a 5% gel. It appears as a doublet.

RNA pellets (made from 50 to 100 μl of a telomerase fraction) are resuspended in 15 μl of sequencing dye (deionized formamide with dye), boiled for a few minutes and quick chilled before loading.

Note:

If a 1 mm thick 6% gel is used, and run overnight, hTR runs at about 1 kb.

If a 0.4 cm thick 5% gel is used, and run at 1000 V (35–40 W), hTR runs at about 450 nt. hTR runs as a single band using this method, but if the fractions are not purified, the samples smear and the signal will be poor.

2. EtBr Staining

Stain the gel for 20–30 min in 0.5 μg/ml of EtBr in 1x TBE to see the snRNP profile.

3. Electroblotting

Genie Transfer apparatus.

The transfer is done onto Hybond N+.

Transfer; rT° in 1x TBE for 0.7 hr, using 0.95 A.

4. Fixing RNA onto Membrane

UV-crosslink using a Stratagene crosslinker; autosetting (120 mj).

Crosslink with the RNA on the membrane face up.

5. Probe

Use either PCR (R3C and U3B primers) to make a radioactive 154 nt fragment, or I hexamer label the 154 nt hTR fragment using Klenow. Probe at 65° C., and the final wash is in 0.1x SSC. Perform blot using Church Protocol (below)

6. Phosphor-Imager Analysis

Expose the blot for 5 hr on a phosphor-imaging plate (e.g., Fuji). The exposure time can be shortened when using concentrated extracts. Film exposure: 2–7 days, depending on the signal.

CHURCH PROTOCOL

Prehybridize in 50 to 100 ml of Church solution (500 mM $Na_2HPO_4$ pH 7.2, 1 m MEDTA, 1% BSA, and 7% SDS). Prehybridize a few hours at 65° C.

Probe with 0.1 µg of $^{32}$P-5' end labelled oligo (forward rxn) (specific activity of probe should be ~$10^8$–$10^9$ cpm/µg). Probe overnight at 65° C.

Remove blot from bag at room temperature and rinse manually in 2× SSC (heated to hybridization T°) twice, for 1 min per wash, 500 ml per wash. This is to quickly get rid of hot label which might non-specifically stick to the membrane.

Wash blot 5×, in 2× (rT°), 0.1% SDS, 5 minutes per wash, 500 ml per wash at rT°.

Wash blot 1×, in 0.1×–2× SSC and 0.1% SDS at hybridizing temp. (500 ml) for 30 min.

Place wet blot on filter paper, wrap with Saran or bag, and expose to film O/N.

Notes:

1. If doing more than one blot, start rinsing the second blot after the first blot is in the second 5 minute wash.

2. Washes for 1 blot: 4 liter; 400 ml 20×SSC and 3600 ml $ddH_2O$. Remove 1 liter and add 15 ml 20% SDS to 3 liter. (2× SSC=300 mM NaCl, therefore about half that of hybridizing salt concentration)

3. Church solution (100 ml): 1 g BSA to 50 ml 1 M $NaPO_4$ pH 7.2, 15 ml $H_2O$, dissolve, then add 0.2 ml 0.5 M EDTA, and 35 ml 20% SDS.

II. PROTOCOLS FOR CRUDE CELL EXTRACT FROM 293 CELLS

This preparation prefers a minimum of $10^7$ cells, either suspension or adherent cells. It can be scaled up for larger numbers of cells proportionally. Preparation of as much as $7.7×10^{10}$ cells has been done with excellent activity but slightly higher background. Furthermore, the whole procedure should be performed at 4° C. and on ice.

Grow cells to midlog phase. Adequate additional cells for counting should be provided: the calculation of buffer amounts is dependent on the number of cells rather than volume.

Either CHAPS or CHAPSO detergent can be used. These show little differences in obtaining active extracts.

A. Buffers

Wash Buffer

| Stock | Final | 20 mL | 100 mL |
| --- | --- | --- | --- |
| 1M HEPES pH 7.5 | 10 mM | 200λ | 1 mL |
| 1M $MgCl_2$ | 1.5 mM | 30λ | 150λ |
| 1M KCl | 10 mM | 200λ | 1 mL |
| 1M DTT | 1 mM | 20λ | 100λ |
| DEPC $H_2O$ | | 19.55 mL | 97.75 mL |

Lysis Buffer (0.5% CHAPS/CHAPSO)

| Stock | Final | 10 mL | 50 mL | 60 mL |
| --- | --- | --- | --- | --- |
| 1M Tris Cl Ph 7.5 | 10 mM | 100λ | 500 µl | 600 µl |
| 1M $MgCl_2$ | 1 mM | 10λ | 50 µl | 60 µl |
| 0.5M EGTA | 1 mM | 20λ | 100 µl | 120 µl |
| 0.1M PMSF | 0.1 mM | 10λ | 50 µl | 60 µl |
| BME | 5 mM | 3λ | 15 | 18 µl |
| 10% Detergent | 0.5% | 500λ | 2500 µl | 3000 µl |
| 100% Glycerol | 10% | 1 mL | 5 mL | 6000 µl |
| DEPC $H_2O$ | | 8.36 mL | 41.785 mL | 50.14 mL |

B. Procedure

1. For adherent cells, grow two sets of 15 cm plates and use one for counting. Once cell count has been determined, rinse the other set twice with 20 mL of cold PBS. Add 10 mL PBS and scrape the cells into a 15 mL centrifuge tube. Continue to step 3.

2. For suspension cultures, grow to a density not exceeding $10^6$ cells/mL (about 6–$7×10^5$/mL is preferred). After establishing cell count, pellet cells in 50 mL centrifuge tubes at 200 g/4° C./5 min. Resuspend in cold PBS equivalent to original volume.

3. Pellet the cells in a clinical centrifuge at 200 g/4° C./5 min. Resuspend thoroughly in Wash Buffer at a concentration of $10^6$ cells/100λ and transfer to microcentrifuge tubes. Spin cells down at 13 k rpm for 1 minute.

4. Remove Wash Buffer and resuspend pellet in detergent lysis buffer at a concentration of $10^6$ cells/18.5λ and transfer to appropriate ultrafuge tube (see below). Leave on ice for 30 min. Parafilm top of tube if deemed necessary.

| Volume | Beckmann Centrifuge Tube | Rotor |
| --- | --- | --- |
| <1 mL | thick-walled micro polyallomer | TLS 55 |
| 1.2 mL | thin-walled micro polyallomer | TLS 55 |
| 2–5 mL | polyallomer | SW 41 |

5. Prepare the proper swinging bucket ultrafuge rotors and chill the appropriate ultracentrifuge to 4° C. For the SW41 rotor, set the XL-80 Ultra at 28.5k rpm for 100,000 g. For the TLS 55 rotor, set the tabletop Ultra at 39k rpm.

6. Spin the lysed cells for 30 minutes.

7. Collect the clear aqueous portion of the supernatant (this is the extract). Aliquot the extract into 100λ portions and freeze on dry ice. Store at −80° C.

III. FOUR STEP METHOD FOR PURIFYING TELOMERASE

A method of making human telomerase that is 3,550-fold purified compared to that in crude cell extracts is described. This method comprises four steps in succession: 1) CHAPS detergent S-100 extract preparation from 293 cells; 2) chromatography of the S-100 extract on POROS® 50 HQ matrix; 3) chromatography of the POROS® 50 HQ active fractions on POROS® 20 Heparin HE-1 matrix; and 4) chromatography of the POROS® 20 Heparin HE-1 active fractions on Oligo 5 affinity matrix. Protocols for each step are provided.

In the first step, $7.3×10^{10}$ 293 cells were collected from 128 liters of suspension culture and CHAPS extracted as described in Example II to yield 883 ml of CHAPS S-100 extract.

In the second step, this extract was subjected to chromatography on a POROS® 50 HQ column, and fractions containing telomerase activity were combined for a total active pool of 72 ml. This step was performed as follows:

POROS® 50 HQ resin (PerSeptive Biosystems, Cambridge, Mass., catalog number 1-2559-05) was resuspended in an equal volume of buffer A (20 mM Hepes pH 7.9, 2 mM $MgCl_2$, 1 mM EGTA, 10% glycerol, 0.1% Nonidet P-40, 1 mM Dithiothreitol, 0.2 mM Phenylmethylsulfonylfluoride, 1 mM Benzamidine, 1 mM Sodium Metabisulfite) equilibrated with 100 mM NaCl (buffer A/100 mM NaCl) and the slurry was packed by gravity in a XK 26/20 chromatography column (Pharmacia, Uppsala, Sweden, catalog number 18-1000-72).

The column was run on a GradiFrac® system (Pharmacia, Uppsala, Sweden, catalog number 13-2192-01). The column was equilibrated with 3 column volumes of buffer A/100 mM NaCl, followed by a high salt wash with 3 column volumes of buffer A/2000 mM NaCl. Finally, the column was re-equilibrated with 3 column volumes of buffer A/100 mM NaCl. Binding capacity of the column was determined by loading increasing amounts of CHAPS extract until telomerase activity was detected in the flow through fractions. Capacity of POROS® 50 HQ was found to be in the range of 20 milligrams of CHAPS extract per milliliter of resin.

1.6 grams of CHAPS extract was loaded on a 80 ml POROS® 50 HQ column at a flow rate of 20 ml/min. The column was then washed with 3 volumes of buffer A/100 mM NaCl. A first elution was performed by washing the column with a 3 column volume medium salt step (buffer A/480 mM NaCl). Telomerase activity was recovered by a high salt step (buffer A/1050 mM NaCl). Fractions from the high salt elution were dialyzed separately against buffer A overnight. Fractions were scanned for telomerase activity by primer elongation assay. Active fractions were pooled. This was repeated several times to process the entire 6.8 grams of CHAPS S-100 extract.

Figure 5:
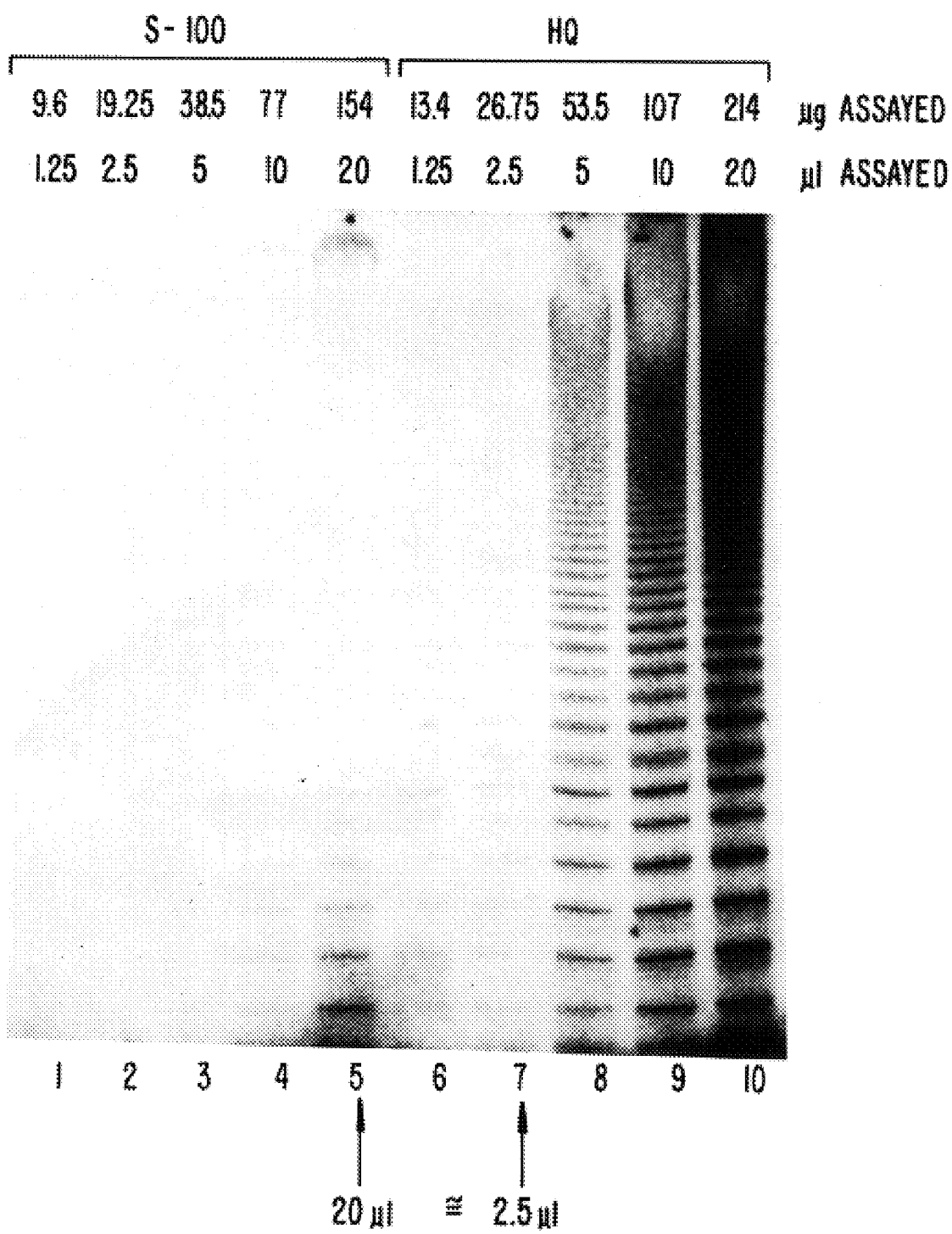
FIG. 5 shows the results of a primer elongation assay from a CHAPS S-100 extract of 293 cells (lanes 1–5) and from the POROS® 50 HQ anion exchange chromatography active pool (lanes 6–10) in the four-step purification procedure.

To determine the relative specific activity of telomerase for the CHAPS S-100 extract and the POROS® 50 HQ active pool, protein concentrations for each were determined (Coomassie Protein Assay Reagent, Pierce Product #23200, Rockford, Ill.), and the preparations were compared for relative telomerase activity by the primer elongation assay described in Example I. (FIG. 5.) The dried gel was exposed to a phosphorimaging screen for 4–16 hr. The screen was scanned and the gray scale adjusted in order to produce an image that appeared linear with respect to the corresponding assay titration. That was usually between 5–25 at the lower end and 1000–2000 at the upper end.

Telomerase activity was measured in arbitrary units and was derived from a visual assessment of the signal resulting from a titration of fractions over a 10–20 fold range in 2-fold increments. Relative comparisons of activity between fractions were determined from the linear range of each titration.

Lanes 1 to 5 of FIG. 5 show primer elongation products from telomerase activity in 1.25 $\mu$l to 20 $\mu$l of the CHAPS S-100 extract; lanes 6 to 10 show the same from a titration of the POROS® 50 HQ active pool. The quantity of telomerase products increases in proportion to the quantity of preparation assayed in lanes 3 to 5 and in lanes 6 to 10, providing a linear range for comparison between the two preparations. From the linear range for each preparation, it was estimated that 20 $\mu$l of the CHAPS S-100 extract (lane 5) generates the same quantity of telomerase primer elongation products as 2.5 $\mu$l of the POROS® 50 HQ active pool (lane 7). Hence, these volumes each contain one arbitrary unit of telomerase activity. This arbitrary unit is only relevant for this particular comparison.

Using the measurements of volume, protein concentration, and volume per telomerase activity unit, simple calculations provide the total units and total protein amount, from which the relative specific activity of telomerase was derived for the two preparations (Table 4). The specific activity of the POROS® 50 HQ active pool (0.037 units/$\mu$g) is 5.8 times greater than that of the CHAPS S-100 extract (0.0065 units/$\mu$g). Therefore, the human telomerase in the POROS® 50 HQ active pool has 5.8-fold increased relative purity compared to that in the CHAPS S-100 extract. The total units of telomerase activity in the POROS® HQ active pool (28,800 units) represents 65% of that in the CHAPS S-100 extract (44,150 units). Therefore, the POROS® HQ chromatography has a yield of 65% for telomerase activity.

In the third step, 24 ml of a POROS® 50 HQ active pool was subjected to chromatography on a POROS® Heparin 20 HE-1 column, and fractions containing telomerase activity were combined for a total active pool of 6 ml. Chromatography was carried out as follows.

POROS® 20 HE-1, was obtained from PerSeptive (Cambridge, Mass., catalog number 1-5229-06). Handling of the resin, packing and equilibration of the column was performed in the exact same way as described for the previous resin, except that a XK 16/20 chromatography column (Pharmacia, Uppsala, Sweden, catalog number 18-8773-01) was used. Binding capacity was determined to be in the range of 15 mg/ml resin.

146.4 milligrams of POROS® 50 HQ pooled material were loaded on a 25 ml POROS® Heparin HE-1 column at a flow rate of 15 ml/min. The column was then washed with 3 volumes of buffer A/100 mM NaCl. A first elution was performed by washing the column with a 3 column volume medium salt step (buffer A/347 mM NaCl). Telomerase activity was recovered by a high salt step (buffer A/1430 mM NaCl). Fractions from the high salt elution were dialyzed separately against buffer A overnight. Fractions were scanned for telomerase activity by primer elongation assay. Active fractions were pooled.

Figure 6:
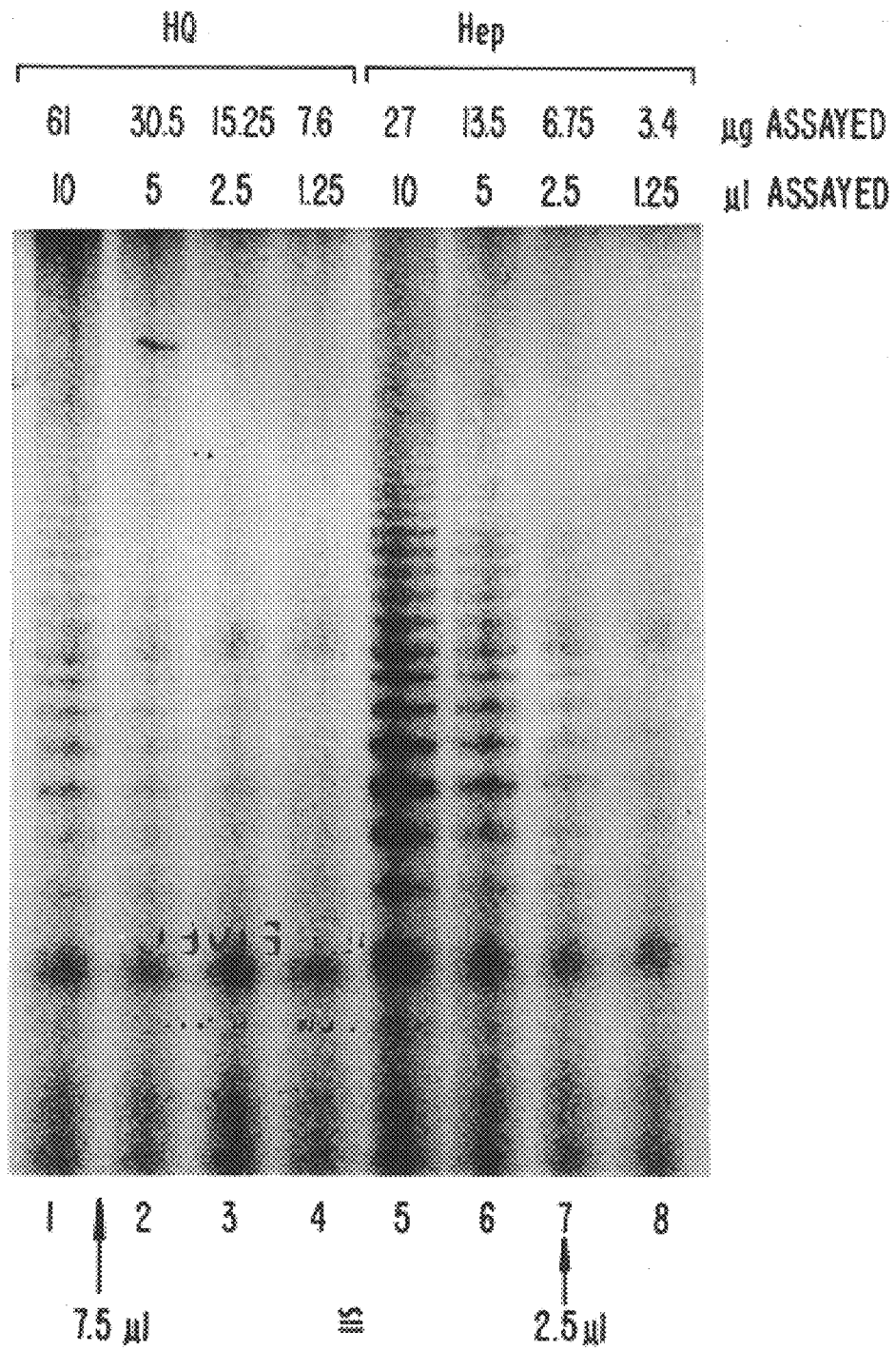
FIG. 6 shows the results of a primer elongation assay from a telomerase preparation from the POROS® 50 HQ anion exchange chromatography active pool (lanes 1–4) and the POROS® Heparin 20 HE-1 chromatography active pool (lanes 5–8) in the four-step purification procedure.

The relative specific activity of telomerase for the POROS® 50 HQ active pool and the POROS® Heparin 20 HE-1 active pool was determined exactly as described above for the previous step. Titrations of the two preparations in the primer elongation assay are shown in FIG. 6; measured and calculated values are shown in Table 4. These data indicate that the human telomerase in the POROS® Heparin 20 HE-1 active pool is 6.8-fold purified compared to that in the POROS® 50 HQ active pool. The cumulative purification after this third step is the product of all previous steps. Hence, the human telomerase in the POROS® Heparin 20 HE-1 active pool has 6.8×5.8=39.4-fold increased relative purity compared to that in the CHAPS S-100 extract. The yield of the POROS® Heparin 20 HE-1 chromatography is 75% for telomerase activity, and the cumulative yield after this third step is 49%.

In the fourth step, 0.14 ml of a POROS® Heparin 20 HE-1 active pool was subjected to chromatography on an affinity matrix using Oligo 5 as the affinity ligand. Fractions from the affinity column that contained telomerase activity were combined for a total active pool of 0.4 ml. Affinity chromatography was performed as follows.

UltraLink® Immobilized NeutrAvidin beads (Pierce, Rockford, Ill., catalog number 53151) were pre-treated with an equal volume of buffer A/100 mM NaCl supplemented with 1 mg/ml BSA, 0.2 mg/ml tRNA and 0.2 mg/ml salmon testes DNA for 1 hour at 4° C. The beads were then rinsed with 5 volumes of buffer A/100 mM NaCl.

Oligo 5, an antisense DNA oligonucleotide (National Biosciences, Inc., Plymouth, Minn.) covering nucleotides 407–436 of the human telomerase RNA was designed with the sequence 5'-*gccgagtcct gggtgcacgt cccatagctc-3' (where *G is biotinylated) (SEQ ID NO:4). Oligo 5 was resuspended at a concentration of 100 µM for use in subsequent experiments.

140 µl of pooled heparin material at a protein concentration of 9 mg/ml was supplemented with 1.6 mM Oligo 5, 2 mM dTTP, 0.1 mM ddATP, 2 mM dGTP, 50 mM Tris HCl pH 7.5, 1 mM Spermidine, 5 mM β-mercaptoethanol, 1 mM MgCl$_2$, 50 mM Potassium Acetate, 1 mM EGTA and incubated at 30° C. for 1 hour. The reaction mixture was added to 400 µl of pre-treated NeutrAvidin beads and mixed at 4° C. for 1–4 hour(s).

The slurry was then poured into a small disposable column and the flow-through was drained off. The flow-through was put back through the column up to three times. The column was then washed with at least 4 column volumes of buffer A/100 mM NaCl and eluted with buffer A/500 mM NaCl. Fractions were tested for telomerase activity by primer elongation assay.

Figure 7:
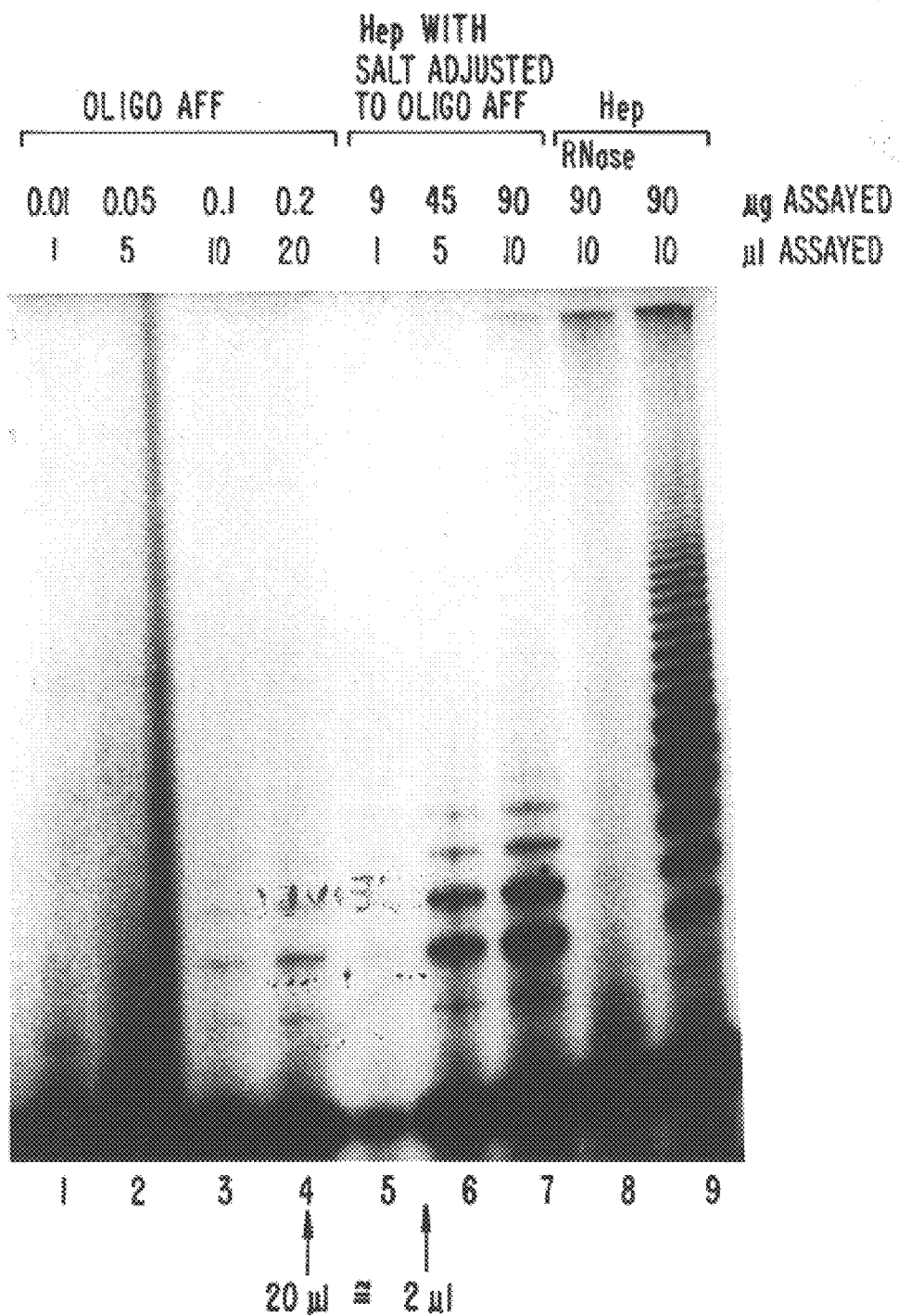
FIG. 7 shows the results of a primer elongation assay from a telomerase preparation from the Oligo 5 affinity isolation active pool (lanes 1–4), the POROS® Heparin 20 HE-1 chromatography active pool adjusted to the salt concentration used for affinity isolation (lanes 5–7), and the POROS® Heparin 20 HE-1 active pool (lanes 8 and 9) in the four-step purification procedure.

The relative specific activity of telomerase for these two preparations was determined exactly as described above for the previous steps with one exception. Telomerase is released from the POROS® 50 HQ, the POROS® Heparin HE-1, and the oligo 5 affinity columns in purification steps 2, 3, and 4 by increasing the salt concentration in the wash buffer. Since salt concentrations over 100 mM inhibit telomerase activity (FIG. 7, compare lanes 7 and 9), the active pools from purification steps 2 and 3 were dialyzed to lower the salt concentration to that of the preparation loaded onto the column for those steps. In purification step 4 (oligo 5 affinity), the pool of active fractions was not desalted. To determine an accurate relative activity, the salt concentration of the preparation loaded onto the affinity column (POROS® Heparin 20 HE-1 active pool) was adjusted to be the same as the Oligo 5 affinity active pool.

Titrations of the two preparations in the primer elongation assay are shown in FIG. 7; measured and calculated values are shown in Table 4. These data indicate that the human telomerase in the Oligo 5 active pool is 90-fold purified compared to that in the POROS® Heparin 20 HE-1 active pool. The cumulative purification after this fourth step is 90×6.8×5.8=3,550. Hence, the human telomerase made by this method has 3,550-fold increased relative purity compared to that in the CHAPS S-100 extract. The yield of the affinity chromatography step is 29% for telomerase activity; the cumulative yield of telomerase activity for this method is 14%.

IV. FIVE STEP METHOD FOR PURIFYING TELOMERASE

A method of making human telomerase that has 32,660-fold increased relative purity compared to that in crude cell extracts is described. This method comprises five steps in succession: 1) CHAPS detergent S-100 extract preparation from 293 cells; 2) chromatography of the S-100 extract on POROS® 50 HQ matrix; 3) chromatography of the POROS® 50 HQ active fractions on POROS® Heparin 20 HE-1 matrix; 4) chromatography of the POROS® Heparin 20 HE-1 active fractions on POROS® spermidine matrix; and 5) chromatography of the POROS® spermidine active fractions on oligonucleotide 5 affinity matrix. Protocols are provided for preparation of the spermidine matrix and running of the spermidine column. Protocols for all other steps were provided in the 4-step method of Example III.

In the 5-step method, the first three steps are the same as in the 4-step method. In the fourth step, 0.7 ml of a POROS® Heparin 20 HE-1 active pool was subjected to chromatography on a freshly prepared (i.e., not commercially available) POROS® spermidine column, and fractions containing telomerase activity were combined for a total active pool of 0.15 ml. Chromatography was performed as follows.

POROS®-Spermidine was prepared in the following manner. Dried POROS® 20 EP (Perseptive 1-6129-03) was placed in coupling buffer (0.1 M sodium phosphate adjusted to pH 10.0 with KOH) to allow beads to hydrate. The hydrated beads were transferred to a disposable column and rinsed with coupling buffer for 20 bed volume. Two bed volumes of a 0.2 M spermidine tetrahydrochloride (Sigma)-0.1 M sodium phosphate were added. The solution of spermidine-coupling buffer was re-adjusted to pH 10. (20 ml of 0.1 M sodium phosphate-0.22 M Spermidine+1.5 ml of 1 N NaOH=0.2 M spermidine-0.1 M sodium phosphate pH 10.0). The beads were rotated with the spermidine solution overnight at room temperature. The spermidine solution was washed off with 20 bed volume of coupling buffer. The remaining reactive groups of the POROS® 20 EP beads were quenched with 2 bed volume of 0.1 M ethanolamine made up in coupling buffer. The mixture was rotated for 2 hours at room temperature. The mixture was washed with 20 bed volumes of coupling buffer. The mixture was washed with 10 bed volume of buffer A/100 mM NaCl and packed into columns for chromatography.

Figure 8:
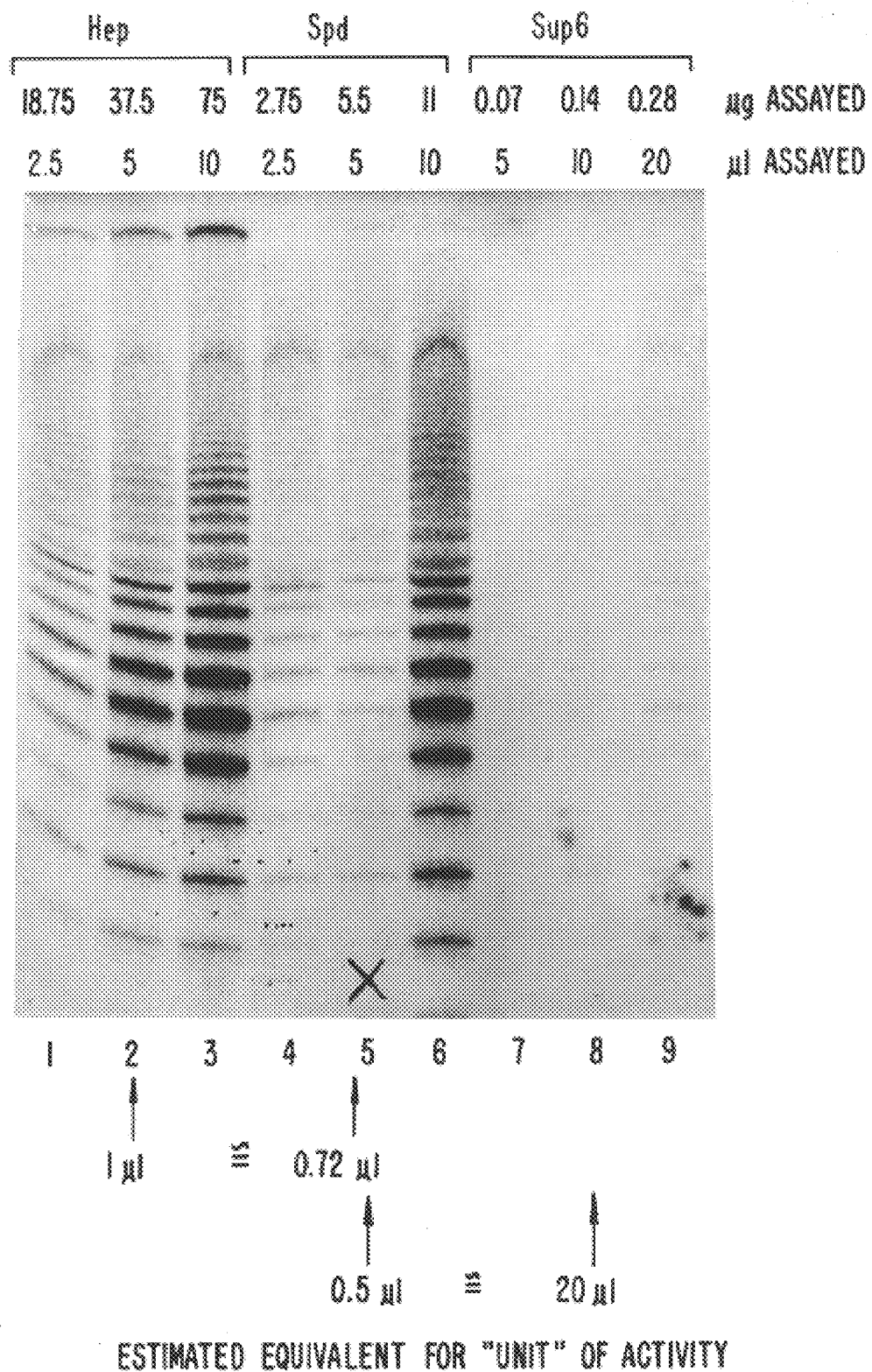
FIG. 8 shows the results of a primer elongation assay from telomerase preparations from the POROS® Heparin 20 HE-1 chromatography active pool (lanes 1–3) and the POROS® Spermidine chromatography active pool (lanes 4–6) in the five-step purification procedure, and from the Superose® 6 active pool (lanes 7–9) in the first six-step assay.

The POROS®-Spermidine column was equilibrated at 4° C. with 10 column volume (CV) of buffer A/100 mM NaCl prior to the application of the sample. The sample POROS® Heparin 20 HE-1 active pool was dialyzed in buffer A to or below 100 mM NaCl) is applied to the column and chromatographed at a flow rate of 0.6 CV per minute. The column was then washed at the same flow rate with 5 CV of buffer A/100 mM NaCl. The proteins were eluted at the same flow rate with the following steps:

–3 CV of buffer A 100 mM KCl-90 mM NaCl
–3 CV of buffer A 150 mM KCl-85 mM NaCl
–3 CV of buffer A 200 mM KCl-80 mM NaCl
–3 CV of buffer A 1000 mM KCl Proteins were eluted at each step, telomerase being essentially eluted from the POROS®-Spermidine column with buffer A/150 mM KCl-85 mM NaCl. The relative specific activity of telomerase for these two preparations was determined. Titrations of the two preparations in the primer elongation assay are shown in FIG. 8; measured and calculated values are shown in Table 5. These data indicate that the human telomerase in the POROS® spermidine active pool is 9.2-fold purified compared to that in the POROS® Heparin 20 HE-1 active pool. The cumulative purification after this fourth step is 9.2×6.8×5.8=363-fold purified compared to the CHAPS S-100 extract. The yield of the POROS® spermidine chromatography is 30% for telomerase activity, and the cumulative yield after these four steps is 14.6%.

Oligo 5 affinity chromatography of POROS® spermidine active fractions purifies human telomerase by a factor of 90 with 29% yield (as it did with POROS® Heparin 20 HE-1 active fractions). Thus, this 5-step method produces human telomerase that has 90×363=32,660-fold increased relative purity compared to that in CHAPS S-100 extracts. The yield of this 5-step method is 4.2%

V. SIX STEP METHOD FOR PURIFYING TELOMERASE

A method of making human telomerase that is 65,320-fold purified compared to that in crude cell extracts is described. This method comprises six steps in succession: 1) CHAPS detergent S-100 extract preparation from 293 cells; 2) chromatography of the S-100 extract on POROS® 50 HQ matrix; 3) chromatography of the POROS® 50 HQ active fractions on POROS® Heparin 20 HE-1 matrix; 4) chromatography of the POROS® Heparin 20 HE-1 active fractions on POROS® spermidine matrix; 5) chromatography of the POROS® Spermidine active fractions on Superose® 6 sizing column; and 6) chromatography of the Superose® 6 sizing column active fractions on Oligo 5 affinity matrix. A protocol for running the Superose® 6 column is provided. Protocols for all other steps were provided previously.

In the 6-step method, the first four steps are the same as in the 5-step method. In the fifth step, 0.02 ml of material from the POROS® spermidine active pool collected in Example IV was subjected to chromatography on a Superose® 6 sizing column, and the fractions containing telomerase activity were combined for a total active pool of 0.16 ml. Superose® 6 chromatography was performed as follows.

The 2.4 ml Superose® 6, PC 3.2/30 column from Pharmacia is pre-equilibrated with 2 CV of buffer A/150 mM NaCl at a flow rate of 40 μl/min. For each Superose® 6 run, 20 ,1 of active POROS® spermidine fraction is loaded on the column which is run at a flow rate of 20 μl/min in buffer A/150 mM NaCl. The bulk of $OD_{280}$ absorbing protein elutes from the column between 1.00 ml and 1.4 ml. The peak of telomerase activity is eluted between 1.4 and 1.6 ml, on the trailing end of the peak of proteins.

The relative specific activity of telomerase for these two preparations was determined. Titrations of the two preparations in the primer elongation assay are shown in FIG. 8; measured and calculated values are shown in Table 5. These data indicate that the human telomerase in the Superose® 6 active pool is 2-fold increased purified compared to that in the POROS® spermidine active pool. The cumulative purification after this fifth step is 2×9.2×6.8×5.8=725.7-fold relative purity compared to the CHAPS S-100 extract. The yield of the Superose® 6 chromatography is 20% for telomerase activity, and the cumulative yield after these five steps is 2.9%.

Oligo 5 affinity chromatography of Superose® 6 active fractions may purify human telomerase to the same extent as for POROS® Heparin 20 HE-1 active fractions. Thus, this 6-step method would produce human telomerase that is 90×725.7=65,320-fold purified compared to that in CHAPS S-100 extracts. The yield of this 6-step method is 0.85%.

VI. SECOND SIX STEP METHOD FOR PURIFYING TELOMERASE

A method of making human telomerase that is over 60,000-fold purified compared to that in crude cell extracts was executed. This method comprises six steps in succession: 1) Dounce homogenization and nuclear extract preparation from 293 cells; 2) chromatography of the nuclear extract on POROS® 50 HQ matrix; 3) chromatography of the POROS® 50 HQ active fractions on POROS® Heparin 20 HE-1 matrix; 4) chromatography of the POROS® Heparin 20 HE-1 active fractions on SOURCE 15Q® matrix; 5) chromatography of the SOURCE 15Q® matrix active fractions on Oligo 14ab affinity matrix and 6) chromatography of the 14ab affinity matrix active fractions on a TSK-Gel*G5000 $PW_{XL}$ sizing column. Protocols for all steps are provided.

A. Preparation Of Nuclear Extract

1. Cells 293 cells are an adenovirus-transformed human embryonic kidney cell line. These cells grow readily in suspension cultures with an optimal harvest density of 0.5×10⁹ cells per liter and doubling time of 24 hours. Cells were obtained from Cellex in the form of wet cell pellets on dry ice. 293 suspension cultures are grown in spinner flasks, and provided in supplies of 2×10¹¹ cells (from 400 liters of culture). The 293 cells are harvested, washed twice in PBS (Ca/Mg free), snap frozen as a wet cell pellet, and shipped on dry ice. (Frozen cells can be stored at −80° C.)

2. Crude Extracts a. Cell pellets are thawed quickly, packed cell volume is measured, then cells are suspended in an equal volume of ice-cold buffer H. Cells are kept on ice and disrupted using a dounce homogenizer fitted with pestle B and 10 up-and-down strokes.

b. Cytoplasm and nuclei are separated by a low speed spin: homogenate is centrifuged for 10 min, 4° C. at 2500 rpm in a Beckman JS4.2 rotor (1780× g). Supernatant is decanted into clean bottles, and pellet is kept on ice for nuclear extract preparation (see below, step j).

Alternative Step b.

If time does not allow for nuclear extract preparation, the nuclear pellet can be stored, but buffer must first be supplemented with glycerol. Measure the volume of homogenate from step a (to be assigned to y variable in the equation below). Add 80% ice-cold glycerol to the homogenate to obtain a final concentration of 10%. Mix well. The volume of 80% glycerol to add, x, can be determined by the equation: x=0.1y/0.7. Centrifuge exactly as in step b. Snap freeze nuclear pellets and store at −80° C. The addition of glycerol does not change any of the following extraction steps.

c. Measure the volume of the supernatant (to be assigned to y variable in the equation below). Add 5 M ice-cold NaCl to the supernatant to obtain a final concentration of 150 mM. Mix well. The volume of 5 M NaCl to add, x, can be determined by the equation: x=0.15y/4.85.

d. Centrifuge supernatant for 1 hour, 4° C. at 40K rpm in a Beckman 45Ti rotor (100K× g). Carefully decant supernatant into a clean container.

e. Measure volume of the supernatant. For every liter of supernatant gradually add 259.5 g solid ammonium sulfate (45% final concentration). Gently mix in the cold room for about 30 min.

f. Collect precipitate by centrifuging mixture for 30 min, 4° C. at 10K rpm in a Sorvall GSA rotor. Decant the supernatant and drain the pellets very well.

g. Resuspend pellets in buffer A containing 50 mM NaCl. Use ⅕ the volume measured in step e (before adding ammonium sulfate) and resuspend pellet using a dounce homogenizer fitted with pestle A.

h. Dialyze in buffer A containing 50 mM NaCl overnight with one change of buffer.

i. Collect the dialysate and centrifuge for 30 min, 4° C. at 15K rpm in a Sorvall SS-34 rotor. Filter the supernatant through Mira-cloth. This is the "crude cytoplasmic extract." It can be snap frozen and stored at −80° C., or loaded directly onto the TosoHaas super Q column. The crude cytoplasmic extract is typically about 230 ml at 25 mg/ml protein and 10 μl is sufficient for telomerase activity in the conventional primer elongation assay.

j. From step b, measure volume of nuclear pellet. Resuspend the nuclei in 0.5 volume of Buffer C.

k. Add slowly while vortexing, another 0.5 packed nuclear volume of buffer C containing 1.2 M NaCl.

l. Dounce homogenize (5 to 10 strokes) with pestle A.

m. Transfer to glass beaker on ice and stir for at least 30 min.

n. Centrifuge for 75 min, 4° C. at 18K rpm in a Sorvall SS-34 rotor.

o. Transfer supernatant to dialysis bags and dialyze overnight or 2×2 hours against hypo buffer containing 100 mM NaCl.

p. Collect the dialysate and centrifuge for 30 min, 4° C. at 15K rpm in a Sorvall SS-34 rotor. Clarified supernatant is the "crude nuclear extract." Snap freeze and store at −80° C. The crude nuclear extract is typically about 650 ml at 7 mg/ml protein and 10 µl is sufficient for telomerase activity in the conventional assay.

B. First Anion Exchange Chromatography

1. The nuclear extract material is subjected to the following ion exchange chromatography. A Poros 50 HQ resin from PerSeptive Biosystems is resuspended in an equal volume of hypo buffer containing 100 mM NaCl and the slurry is packed by gravity in a XK 50/30 chromatography column (Pharmacia).

2. The column is run on a GradiFrac system (Pharmacia) after being equilibrated with 3 column volumes of hypo buffer containing 100 mM NaCl followed by a high salt wash with 3 column volumes of hypo buffer containing 2000 mM NaCl. The column is then re-equilibrated with 3 column volumes of hypo buffer containing 100 mM NaCl. Capacity of the resin for telomerase is in the range of 20 mg of nuclear extract per milliliter of resin.

3. In a typical preparation starting with $2 \times 10^{11}$ cells (600 grams of cells), 650–700 ml of crude nuclear extract or approximately 4.7 grams of proteins are loaded on a 300 ml column at a flow rate of 20 ml/min. The column is then washed with 3 column volumes of hypo buffer containing 100 mM NaCl. A medium-salt wash step is performed with 3 column volumes of hypo buffer containing 404 mM NaCl. Telomerase activity is recovered by a high-salt elution with hypo buffer containing 1050 mM NaCl. Fractions from the high-salt elution are dialyzed separately against hypo buffer containing 50 mM NaCl overnight and scanned for telomerase activity by conventional assay before being pooled and subjected to the next purification step.

C. Heparin Chromatography 1. 100–120 ml of combined active fractions from the previous step, or approximately 660 milligrams of proteins are loaded on a 60 ml Poros Heparin 20 HE-1 column from PerSeptive Biosystems at a flow rate of 8 ml/min. Handling of the resin, packing and equilibration of the column is performed in the same way as described for the previous resin, except that an XK 26/20 chromatography column (Pharmacia) is used and that binding capacity for this column is in the range of 15 mg/ml of resin. The column is then washed with 3 column volumes of hypo buffer containing 100 mM NaCl. A medium-salt wash step is performed with 3 column volumes of hypo buffer containing 290 mM NaCl. Telomerase activity is recovered by a high-salt elution with hypo buffer containing 1430 mM NaCl. Fractions from the high-salt elution are dialyzed separately against hypo buffer containing 250 mM NaCl overnight and scanned for telomerase activity by conventional assay before being pooled and subjected to the next purification step.

D. Second Anion Exchange Chromatography 1. 20–40 ml of combined active fractions from the previous step, or approximately 240 milligrams of proteins are diluted 1:1 with hypo buffer prior to being loaded on a 16 ml Source 15Q column from Pharmacia. The column is usually run at maximum binding capacity at a flow rate of 5 ml/min on an FPLC (Pharmacia). Depending on the number of fractions pooled from the previous step, two consecutive runs are required. Handling of the resin, packing and equilibration of the column is performed in the same way as described for the previous resin, except that an HR 16/10 chromatography column (Pharmacia) is used and that binding capacity for this column is in the range of 10 mg/ml of resin. The column is then washed with 3 column volumes of hypo buffer containing 100 mM NaCl. A medium-salt wash step is performed with 3 column volumes of hypo buffer containing 307 mM NaCl. Telomerase activity is recovered by a high-salt elution with hypo buffer containing 1000 mM NaCl. Fractions from the high-salt elution are scanned for telomerase activity by conventional assay before being pooled and subjected to affinity chromatography.

Starting with nuclear extract from $2 \times 10^{11}$ cells, this partial purification scheme yields 10 ml at 10 mg/ml protein and 2 µl is sufficient for telomerase activity in the conventional assay. Relative purity of telomerase is 100 fold over the crude extract with about a 30% yield. The telomerase concentration, by quantitative RNA analysis, is 0.3 pmoles/ml. This material is suitable for affinity chromatography.

Buffers

Buffer H—10 mM HEPES-KOH, pH 7.9; 2 mM $MgCl_2$; 1 mM EGTA; 10 mM KCl Add just before use: 1 mM DTT; 1 mM Sodium Metabisulfite; 1 mM Benzamidine and 0.2 mM PMSF Buffer A—20 mM HEPES-KOH, pH 7.9; 1 mM $MgCl_2$; 1 mM EGTA; 10% glycerol Adjust before use: 1 mM DTT; 1 mM Sodium Metabisulfite; 1 mM Benzamidine; 0.2 mM PMSF; and 5 µg/ml Leupeptin Buffer C—20 mM HEPES-KOH, pH 7.9; 1.5 mM $MgCl_2$; 0.5 mM EGTA; 20 mM; NaCl; 25% glycerol Add just before use: 1 mM DTT; 1 mM Sodium Metabisulfite; 1 mM Benzamidine; and 0.1 mM PMSF Hypo Buffer—20 mM HEPES-KOH, pH 7.9; 2 mM $MgCl_2$; 1 mM EGTA; 10% glycerol; 0.1% NP-40

Add just before use: 1 mM DTT; 1 mM Sodium Metabisulfite; 1 mM Benzamidine; and 0.2 mM PMSF

E. Affinity Chromatography

485 µl of Source 15Q active pool at a protein concentration of approximately 7 mg/ml were supplemented with 100 µg of poly dT oligonucleotide (30-mer), 125 µg of polyuridylic acid (Sigma, St. Louis, Mo., catalog number P-9528) and 500 picomoles of oligonucleotide 14ab as ligand (2'-O-methyl, biotinylated, disulfide linked, RNA oligonucleotide, Yale University, New Haven, Conn.) in a total volume of 500 µl. Oligo 14ab has the sequence 5'-cgttcctctt cctgcggcct-3' (Oligo 14ab) (SEQ ID NO:7) and covers nucleotides 361–380 the human telomerase RNA.

After a 30 minute incubation at room temperature, the mixture is added to 4–6×10⁶ particles of MPG® Streptavidin beads (CPG, Lincoln Park, N.J., catalog number MSTR0510) equilibrated with buffer A/700 mM NaCl and the beads were allowed to sediment for approximately 10 minutes. The beads were then subjected to magnetic separation, the supernatant was discarded and the beads were washed with 100 μl of buffer A/700 mM NaCl. The beads were resuspended in 20 μl elution buffer (Buffer A supplemented with 500 mM Tris HCl pH 8.3 and 100 mM DTT) and incubated at room temperature for 20 minutes with frequent resuspension. The beads were again subjected to magnetic separation, the supernatant containing telomerase activity was collected and used as is for subsequent purification.

F. Gel Exclusion Size Chromatography

Tracking telomerase activity using size exclusion chromatograph can be performed on affinity purified material. The eluted material (150 μl, 2 fmol telomerase/μl) from 14ab affinity chromatography is applied to a TSK-Gel*G5000PW$_{XL}$ column (30 cm×7.8 mm, TosoHaas), already equilibrated in buffer 'B'. The column is eluted in the same buffer at a flow rate of 250 μl/min. Telomerase activity profiles and hTR quantities are determined for the various fractions. Enzymatic activity as well as hTR concentrations peak between 7.0 ml and 7.4 ml of eluent. Buffer 'B': 0.2 M Triethylamine-$CO_2$; 1 mM EGTA; 1 mM DTT; 1 mM $MgCl_2$; 1% Glycerol G. Amino Acid Sequence Analysis The amino acid sequences of peptide fragments of b120 and y105 are determined as follows. Acrylamide gels were prepared using standard protocols and stained with silver stain. In gel reduction, acetamidation and tryptic digestion were similar to published procedures (Jeno et al., *Analyt. Biochem.* 224, 451–455 (1995); Rosenfeld, et al., *Analyt. Biochem.* 203, 173–179 (1992)). After washing with 100 mM $NH_4HCO_3$ and acetonitrile, gel pieces were swollen in the digestion buffer containing 50 mM $NH_4HCO_3$, 5 mM $CaCl_2$ and 12.5 ng$\mu l^{-1}$ trypsin (Boehringer Mannheim, sequencing grade) at 4° C. After 45 min, the supernatant was aspirated and replaced with 5–10 μl of the same buffer without trypsin to keep gel pieces wet during enzymatic cleavage (37° C., overnight).

Peptides were extracted by three changes of 5% formic acid and acetonitrile and dried down. Approximately 100 nl of POROS R2 sorbent (Perseptive Biosystems) was placed in the tip of a pulled GC 100F-10 (CEI, Pangbourne) capillary. Note that the resin is not packed, and that no frit or other micro LC assembling is necessary. A new capillary and a new portion of resin are used for each analysis to avoid cross-contaminations even at the femtomole level. Dried peptide mixture was dissolved in 10 μl 5% formic acid, loaded onto the pre-equilibrated capillary, washed and eluted with 60% methanol in 5% formic acid into the spraying capillary. The elution volume is 10-fold larger than the resin volume, resulting in good peptide recovery.

Nano-electrospray is performed on an API III (Perkin-Elmer Sciex, Ontario, Canada) mass spectrometer as described (Wilm et al., *Analyt. Chem.* 68:1–8 (1996); Mann et al., *Analyt. Chem.* 66, 4390–4399 (1994)). For precursor ion selection, quadrupole 1 was set to transmit a mass window of 2 Da. Step size for the tandem mass spectra was 0.2 Da, and resolution was set so that fragment masses could be assigned to better than 1 Da.

Genbank was searched to identify polypeptides containing the amino acid sequences of the y105 and b120 fragments. Nucleolin (Genbank M60858 J05584) contained sequences from y105 and elongation factor 2 homolog (Genbank D21163) contained sequences from b120.

The present invention provides novel methods for purifying telomerase. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

TABLE 4

PURIFICATION TABLE FOR 4 STEP METHOD

| Step | | Vol. | Prot. Conc. | Total Prot. | μl per "unit activity" | Total Units | Sp. Act. Units/μg | Purification Step | Cum. | Yield Step | Cum. |
|---|---|---|---|---|---|---|---|---|---|---|---|
| 1 | CHAPS S-100 | 883 ml | 7.7 mg/ml | 6799.1 mg | 20 μl | 44,150 | 0.0065 | 1 | 1 | 100% | 100% |
|   | ↓ | | | | | | | | | | |
| 2 | HQ | 72 ml | 10.7 mg/ml | 770.4 mg | 2.5 μl | 28,800 | 0.037 | 5.8x | 5.8 x | 65% | 65% |
|   |   | 24 ml | 6.1 mg/ml | 146.4 mg | 7.5 μl | 3200 | 0.0219 | | | | |
|   | ↓ | | | | | | | | | | |
| 3 | Hep | 6 ml | 2.7 mg/ml | 16.2 mg | 2.5 μl | 2400 | 0.148 | 6.8x | 39.4 x | 75% | 48.8% |
|   |   | 140 μl | 9 mg/ml | 1260 μg | 2 μl | 70 | 0.056 | | | | |
|   | ↓ | | | | | | | | | | |
| 4 | Oligo 5 Affin | 400 μl | 0.01 mg/ml | 4 μg | 20 μl | 20 | 5 | 90 x | 3,550x | 29% | 1% |

TABLE 5

PURIFICATION BY POROS ® SPERMIDINE AND Superose ® 6

|  | vol. | prot. conc. | total prot. | µl per unit activity | total units | sp. act. units/µg | purification | yield |
|---|---|---|---|---|---|---|---|---|
| Hep | 700 µl | 7.5 mg/ml | 5250 µg | 1 µl | 700 u | 0.133 | | |
| Spd | 150 µl | 1.13 mg/ml | 169.5 µg | 0.72 µl | 208.3 u | 1.23 | 9.2 x | 30% |
|  | 20 µl | 1.1 mg/ml | 22 µg | 0.5 µl | 40 u | 1.82 | | |
| Sup6 | 160 µl | 0.014 mg/ml | 2.24 µg | 20 µl | 8 u | 3.57 | 2 x | 20% |

What is claimed is:

1. A composition comprising human telomerase having at least 2,000-fold increased relative purity compared with crude extract of cells from adenovirus-transformed kidney cell line (293 cells).

2. The composition of claim 1 wherein telomerase has at least 60,000-fold increased relative purity.

3. A composition comprising human telomerase having at least 60,000-fold increased relative purity compared with crude extract of cells from adenovirus-transformed kidney cell line (293 cells)produced by steps of:

(a) contacting telomerase from an impure composition containing organic biopolymers with a first matrix that binds molecules bearing a negative charge, separating telomerase from other organic biomolecules that do not bind to the matrix and collecting the telomerase;

(b) contacting the telomerase with a matrix that binds molecules bearing a positive charge, separating telomerase from other organic biomolecules that do not bind to the matrix and collecting the telomerase;

(c) contacting the telomerase with a second matrix that binds molecules bearing a negative charge, separating telomerase from other organic biomolecules that do not bind to the matrix and collecting the telomerase;

(d) contacting the telomerase with an affinity agent having specific affinity for telomerase, separating telomerase from other organic biomolecules that do not bind to the affinity agent and collecting the telomerase;

(e) separating the telomerase from other organic biomolecules according to molecular size, shape, or buoyant density and collecting the telomerase.

4. The composition of claim 3 wherein the impure composition is a nuclear extract of cells from adenovirus-transformed kidney cell line (293 cells), the first matrix that binds molecules bearing a negative charge is POROS® 50 HQ, the matrix binding molecules bearing a positive charge is POROS® Heparin 20 HE-1, the second matrix that binds molecules bearing a negative charge is SOURCE 15Q®, the affinity agent comprises an oligonucleotide comprising the sequence 5'-cgttcctctt cctgcggcct-3' (SEQ ID NO:7), and the step of separating comprises separating according to size on a TosoHaas TSK-Gel*G5000PW$_{XL}$ sizing column.

5. The composition of claim 1 wherein telomerase has at least 20,000-fold increased relative purity.

6. A composition comprising human telomerase having at least 20,000-fold increased relative purity compared with crude extract of cells from adenovirus-transformed kidney cell line (293 cells) produced by steps of:

(a) contacting telomerase from an impure composition containing organic biopolymers with a first matrix that binds molecules bearing a negative charge, separating telomerase from other organic biomolecules that do not bind to the matrix and collecting the telomerase;

(b) contacting the telomerase with a matrix that binds molecules bearing a positive charge, separating telomerase from other organic biomolecules that do not bind to the matrix and collecting the telomerase;

(c) contacting the telomerase with an intermediate-selectivity matrix, separating telomerase from other organic biomolecules that do not bind to the matrix and collecting the telomerase; and (d) contacting the telomerase with an affinity agent having specific affinity for telomerase, separating telomerase from other organic biomolecules that do not bind to the affinity agent and collecting the telomerase.

7. The composition of claim 6 wherein the impure composition is a nuclear extract of cells from adenovirus-transformed kidney cell line (293 cells), the first matrix that binds molecules bearing a negative charge is POROS® 50 HQ, the matrix binding molecules bearing a positive charge is POROS® Heparin 20 HE-1, the intermediate-specificity matrix comprises spermidine and the affinity agent comprises an oligonucleotide comprising the sequence 5'-gccgagtcct gggtgcacgt cccatagct c-3' (SEQ ID NO:4).

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 981 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: -
      (B) LOCATION: 1..981
      (D) OTHER INFORMATION: /note= "PstI fragment of the 2.4 kb
          SauIIIA1-HindIII fragment of clone 28-1"

(xi) SEQUENCE DESCRIPTION: SEQ ID NO:1:

```
CTGCAGAGGA TAGAAAAAAG WCCCTCTGAT ACCTCAAGTT AGTTTCACCT TTAAAGAAGG       60

TCGGAAGTAA AGACGCAAAG CCTTTCCCGG ACGTGCGGAA GGGCAACGTC CTTCCTCATG      120

GCCGGAAATG GAACTTTAAT TTCCCGTTCC CCCCAACCAG CCCGCCCGAG AGAGTGACTC      180

TCACGAGAGC CGCGAGAGTC AGCTTGGCCA ATCCGTGCGG TCGGCGGCCG CTCCCTTTAT      240

AAGCCGACTC GCCCGGCAGC GCACCGGGTT GCGGAGGGTG GGCCTGGGAG GGTGGTGGC      300

CATTTTTTGT CTAACCCTAA CTGAGAAGGG CGTAGGCGCC GTGCTTTTGC TCCCCGCGCG      360

CTGTTTTTCT CGCTGACTTT CAGCGGGCGG AAAAGCCTCG GCCTGCCGCC TTCCACCGTT      420

CATTCTAGAG CAAACAAAAA ATGTCAGCTG CTGGCCCGTT CGCCCCTCCC GGGGACCTGC      480

GGCGGGTCGC CTGCCCAGCC CCCGAACCCC GCCTGGAGGC CGCGGTCGGC CCGGGGCTTC      540

TCCGGAGGCA CCCACTGCCA CCGCGAAGAG TTGGGCTCTG TCAGCCGCGG GTCTCTCGGG      600

GGCGAGGGCG AGGTTCAGGC CTTTCAGGCC GCAGGAAGAG GAACGGAGCG AGTCCCCGCG      660

CGCGGCGCGA TTCCCTGAGC TGTGGGACGT GCACCCAGGA CTCGGCTCAC ACATGCAGTT      720

CGCTTTCCTG TTGGTGGGGG GAACGCCGAT CGTGCGCATC CGTCACCCCT CGCCGGCAGT      780

GGGGGCTTGT GAACCCCCAA ACCTGACTGA CTGGGCCAGT GTGCTGCAAA TTGGCAGGAG      840

ACGTGAAGGC ACCTCCAAAG TCGGCCAAAA TGAATGGGCA GTGAGCCGGG GTTGCCTGGA      900

GCCGTTCCTG CGTGGGTTCT CCCGTCTTCC GCTTTTTGTT GCCTTTTATG GTTGTATTAC      960

AACTTAGTTC CTGCTCTGCA G                                               981
```

(2) INFORMATION FOR SEQ ID NO:2:

(i) SEQUENCE CHARACTERISTICS:

```
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5' biotinylated guanosine"

(ix) FEATURE:
            (A) NAME/KEY: -
            (B) LOCATION: 1..30
            (D) OTHER INFORMATION: /note= "oligonucleotide anti-P"

(xi) SEQUENCE DESCRIPTION: SEQ ID NO:2:

NCCTACGCCC TTCTCAGTTA GGGTTAGACA                                      30

(2) INFORMATION FOR SEQ ID NO:3:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5' biotinylated cytidine"

(ix) FEATURE:
            (A) NAME/KEY: -
            (B) LOCATION: 1..22
            (D) OTHER INFORMATION: /note= "oligonucleotide P3"

(xi) SEQUENCE DESCRIPTION: SEQ ID NO:3:

NGCCCTTCTC AGTTAGGGTT AG                                              22

(2) INFORMATION FOR SEQ ID NO:4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5' biotinylated guanosine"

(ix) FEATURE:
            (A) NAME/KEY: -
            (B) LOCATION: 1..30
            (D) OTHER INFORMATION: /note= "Oligo 5"

(xi) SEQUENCE DESCRIPTION: SEQ ID NO:4:

NCCGAGTCCT GGGTGCACGT CCCATAGCTC                                      30

(2) INFORMATION FOR SEQ ID NO:5:

(i) SEQUENCE CHARACTERISTICS:
            (A) LENGTH: 30 base pairs
            (B) TYPE: nucleic acid
```

(C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5' biotinylated guanosine"

(ix) FEATURE:
            (A) NAME/KEY: -
            (B) LOCATION: 1..30
            (D) OTHER INFORMATION: /note= "Oligo 13"

(xi) SEQUENCE DESCRIPTION: SEQ ID NO:5:

NAACGGGCCA GCAGCTGACA TTTTTTGTTT                                    30

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                /note= "N = 5' biotinylated guanosine"

(ix) FEATURE:
            (A) NAME/KEY: -
            (B) LOCATION: 1..30
            (D) OTHER INFORMATION: /note= "Oligo 14"

(xi) SEQUENCE DESCRIPTION: SEQ ID NO:6:

NCTCTAGAAT GAACGGTGGA AGGCGGCAGG                                    30

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note= "Oligo 14ab"

(xi) SEQUENCE DESCRIPTION: SEQ ID NO:7:

CGTTCCTCTT CCTGCGGCCT                                               20

(2) INFORMATION FOR SEQ ID NO:8:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

TTAGGGTTAG GGTTAGGG                                                 18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

CCCTAACCCT AACCCTAA                                                18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5' biotinylated adenosine"

(ix) FEATURE:
        (A) NAME/KEY: -
        (B) LOCATION: 1..18
        (D) OTHER INFORMATION: /note= "oligonucleotide M2/TS"

(xi) SEQUENCE DESCRIPTION: SEQ ID NO:10:

NATCCGTCGA GCAGAGTT                                                18

(2) INFORMATION FOR SEQ ID NO:11:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..28
        (D) OTHER INFORMATION: /note= "peptide GP 80A"

(xi) SEQUENCE DESCRIPTION: SEQ ID NO:11:

Cys Arg Lys Lys Thr Met Phe Arg Tyr Leu Ser Val Thr Asn Lys Gln
1              5                   10                 15

Lys Trp Asp Gln Thr Lys Lys Lys Arg Lys Glu Asn
            20                 25

(2) INFORMATION FOR SEQ ID NO:12:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..24

(D) OTHER INFORMATION: /note= "peptide GP 80B"

(xi) SEQUENCE DESCRIPTION: SEQ ID NO:12:

Cys His Ile Ser Glu Pro Lys Glu Arg Val Tyr Lys Ile Leu Gly Lys
1               5                   10                  15

Lys Tyr Pro Lys Thr Glu Glu Glu
                20

(2) INFORMATION FOR SEQ ID NO:13:

(i) SEQUENCE CHARACTERISTICS:
       (A) LENGTH: 22 amino acids
       (B) TYPE: amino acid
       (C) STRANDEDNESS:
       (D) TOPOLOGY: linear (ii) MOLECULE TYPE: peptide (ix) FEATURE:
       (A) NAME/KEY: Peptide
       (B) LOCATION: 1..22
       (D) OTHER INFORMATION: /note= "peptide GP 95A"

(xi) SEQUENCE DESCRIPTION: SEQ ID NO:13:

Asp Asn Asn Leu Cys Ile Leu Ala Leu Leu Arg Phe Leu Leu Ser Leu
1               5                   10                  15

Glu Arg Phe Asn Ile Leu
                20

(2) INFORMATION FOR SEQ ID NO:14:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: 1
       (D) OTHER INFORMATION: /mod_base= OTHER
           /note= "N = 5' biotinylated cytidine"

(ix) FEATURE:
       (A) NAME/KEY: -
       (B) LOCATION: 1..20
       (D) OTHER INFORMATION: /note= "biotinylated Oligo 14ab"

(xi) SEQUENCE DESCRIPTION: SEQ ID NO:14:

NGTTCCTCTT CCTGCGGCCT                                            20

(2) INFORMATION FOR SEQ ID NO:15:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: modified_base
       (B) LOCATION: 1
       (D) OTHER INFORMATION: /mod_base= OTHER
           /note= "N = 5' biotin disulfide-linked
           to thymidine (biotin-SS-T)"

-continued (xi) SEQUENCE DESCRIPTION: SEQ ID NO:15:

NTAGGGTTAG GGTTAGGG                                                      18